(12) United States Patent
Johnston

(10) Patent No.: US 8,305,432 B2
(45) Date of Patent: Nov. 6, 2012

(54) SCANNING BEAM DEVICE CALIBRATION

(75) Inventor: Richard S. Johnston, Sammamish, WA (US)

(73) Assignee: University of Washington, Seattle, WA (US)

( * ) Notice: Subject to any disclaimer, the term of this patent is extended or adjusted under 35 U.S.C. 154(b) by 1608 days.

(21) Appl. No.: 11/652,411

(22) Filed: Jan. 10, 2007

(65) Prior Publication Data
US 2008/0165360 A1 Jul. 10, 2008

(51) Int. Cl.
*H04N 7/18* (2006.01)
*G01B 11/00* (2006.01)

(52) U.S. Cl. ............... 348/65; 348/67; 348/68; 356/394

(58) Field of Classification Search .................. None
See application file for complete search history.

(56) References Cited

U.S. PATENT DOCUMENTS

| | | |
|---|---|---|
| 3,470,320 A | 9/1969 | Pike et al. |
| 3,644,725 A | 2/1972 | Lochridge, Jr. |
| 4,206,495 A | 6/1980 | McCaslin |
| 4,234,788 A | 11/1980 | Palmer et al. |
| 4,264,208 A | 4/1981 | Haberl et al. |
| 4,710,619 A | 12/1987 | Haberl |
| 4,743,283 A | 5/1988 | Borsuk |
| 4,768,513 A | 9/1988 | Suzuki |
| 4,770,185 A | 9/1988 | Silverstein et al. |
| 4,782,228 A | 11/1988 | Westell |
| 4,821,117 A | 4/1989 | Sekiguchi |
| 4,831,370 A | 5/1989 | Smoot |
| 4,872,458 A | 10/1989 | Kanehira et al. |
| 4,948,219 A | 8/1990 | Seino et al. |
| 4,963,018 A | 10/1990 | West |
| 5,081,350 A | 1/1992 | Iwasaki et al. |
| 5,144,421 A * | 9/1992 | Lemelson ............ 348/91 |
| 5,172,685 A | 12/1992 | Nudelman |
| 5,178,130 A | 1/1993 | Kaiya |
| 5,185,835 A | 2/1993 | Vial et al. |
| 5,315,383 A | 5/1994 | Yabe et al. |
| 5,360,968 A | 11/1994 | Scott |
| 5,454,807 A | 10/1995 | Lennox et al. |
| 5,455,669 A | 10/1995 | Wetteborn |

(Continued)

FOREIGN PATENT DOCUMENTS

EP 1077360 2/2001

(Continued)

OTHER PUBLICATIONS

Aloisi et al., "Electronic Linearization of Piezoelectric Actuators and Noise Budget in Scanning Probe Microscopy", Review of Scientific Instruments, vol. 77, No. 7, Jul. 5, 2006, pp. 073701-1 through 073701-6.

(Continued)

*Primary Examiner* — Lin Ye
*Assistant Examiner* — John H Morehead, III
(74) *Attorney, Agent, or Firm* — Blakely, Sokoloff, Taylor & Zafman

(57) ABSTRACT

Scanning beam device calibration using a calibration pattern is disclosed. In one aspect, a method may include acquiring an image of a calibration pattern using a scanning beam device. The acquired image may be compared with a representation of the calibration pattern. The scanning beam device may be calibrated based on the comparison. Software and apparatus to perform these and other calibration methods are also disclosed.

25 Claims, 11 Drawing Sheets

U.S. PATENT DOCUMENTS

| | | | |
|---|---|---|---|
| 5,459,570 A | 10/1995 | Swanson et al. | |
| 5,557,444 A | 9/1996 | Melville et al. | |
| 5,596,339 A | 1/1997 | Furness, III et al. | |
| 5,627,922 A | 5/1997 | Koelman et al. | |
| 5,664,043 A | 9/1997 | Donaldson et al. | |
| 5,694,237 A | 12/1997 | Melville | |
| 5,695,491 A | 12/1997 | Silverstein | |
| 5,701,132 A | 12/1997 | Kollin et al. | |
| 5,751,465 A | 5/1998 | Melville et al. | |
| 5,784,098 A | 7/1998 | Shoji et al. | |
| 5,822,073 A | 10/1998 | Yee et al. | |
| 5,822,486 A | 10/1998 | Svetkoff et al. | |
| 5,887,009 A | 3/1999 | Mandella et al. | |
| 5,894,122 A | 4/1999 | Tomita | |
| 5,903,397 A | 5/1999 | Melville et al. | |
| 5,913,591 A | 6/1999 | Melville | |
| 5,939,709 A | 8/1999 | Ghislain et al. | |
| 5,969,871 A | 10/1999 | Tidwell et al. | |
| 5,982,528 A | 11/1999 | Melville | |
| 5,982,555 A | 11/1999 | Melville et al. | |
| 5,991,048 A | 11/1999 | Karlson et al. | |
| 5,995,264 A | 11/1999 | Melville | |
| 6,046,720 A | 4/2000 | Melville et al. | |
| 6,049,407 A | 4/2000 | Melville | |
| 6,061,163 A | 5/2000 | Melville | |
| 6,069,698 A | 5/2000 | Ozawa et al. | |
| 6,069,725 A | 5/2000 | Melville | |
| 6,097,353 A | 8/2000 | Melville et al. | |
| 6,154,321 A | 11/2000 | Melville et al. | |
| 6,157,352 A | 12/2000 | Kollin et al. | |
| 6,166,841 A | 12/2000 | Melville | |
| 6,191,761 B1 | 2/2001 | Melville et al. | |
| 6,204,832 B1 | 3/2001 | Melville et al. | |
| 6,220,711 B1 | 4/2001 | Melville et al. | |
| 6,243,186 B1 | 6/2001 | Melville et al. | |
| 6,257,727 B1 | 7/2001 | Melville | |
| 6,263,234 B1 | 7/2001 | Engelhardt et al. | |
| 6,281,862 B1 | 8/2001 | Tidwell et al. | |
| 6,285,505 B1 | 9/2001 | Melville et al. | |
| 6,288,816 B1 | 9/2001 | Melville et al. | |
| 6,291,819 B1 | 9/2001 | Hartley | |
| 6,294,775 B1 | 9/2001 | Seibel et al. | |
| 6,317,548 B1 | 11/2001 | Rockwell et al. | |
| 6,369,953 B2 | 4/2002 | Melville et al. | |
| 6,388,641 B2 | 5/2002 | Tidwell et al. | |
| 6,411,838 B1 | 6/2002 | Nordstrom et al. | |
| 6,441,359 B1 | 8/2002 | Cozier et al. | |
| 6,492,962 B2 | 12/2002 | Melville et al. | |
| 6,535,183 B2 | 3/2003 | Melville et al. | |
| 6,538,625 B2 | 3/2003 | Tidwell et al. | |
| 6,560,028 B2 | 5/2003 | Melville et al. | |
| 6,563,105 B2 | 5/2003 | Seibel et al. | |
| 6,581,445 B1 | 6/2003 | Weiss | |
| 6,627,903 B1 | 9/2003 | Hirayanagi | |
| 6,700,552 B2 | 3/2004 | Kollin et al. | |
| 6,734,835 B2 | 5/2004 | Tidwell et al. | |
| 6,747,753 B1 | 6/2004 | Yamamoto | |
| 6,845,190 B1 * | 1/2005 | Smithwick et al. | 385/25 |
| 6,850,673 B2 | 2/2005 | Johnston, II et al. | |
| 6,856,712 B2 | 2/2005 | Fauver et al. | |
| 6,867,753 B2 | 3/2005 | Chinthammit et al. | |
| 6,959,130 B2 | 10/2005 | Fauver et al. | |
| 6,975,898 B2 | 12/2005 | Seibel | |
| 6,977,631 B2 | 12/2005 | Melville et al. | |
| 7,068,878 B2 | 6/2006 | Crossman-Bosworth et al. | |
| 7,123,790 B2 | 10/2006 | Rosman et al. | |
| 7,159,782 B2 * | 1/2007 | Johnston et al. | 235/462.45 |
| 7,184,150 B2 | 2/2007 | Qualing et al. | |
| 7,189,961 B2 | 3/2007 | Johnston et al. | |
| 7,190,329 B2 * | 3/2007 | Lewis et al. | 345/7 |
| 7,230,583 B2 | 6/2007 | Tidwell et al. | |
| 7,252,236 B2 | 8/2007 | Johnston et al. | |
| 7,277,819 B2 | 10/2007 | Marcus et al. | |
| 7,982,765 B2 * | 7/2011 | Lewis et al. | 348/98 |
| 2001/0051761 A1 | 12/2001 | Khadem | |
| 2001/0055462 A1 | 12/2001 | Seibel | |
| 2002/0010384 A1 | 1/2002 | Shahidi et al. | |
| 2002/0062061 A1 | 5/2002 | Kaneko et al. | |
| 2002/0064341 A1 | 5/2002 | Fauver et al. | |
| 2002/0080359 A1 | 6/2002 | Denk et al. | |
| 2002/0093467 A1 | 7/2002 | Tidwell et al. | |
| 2002/0093563 A1 | 7/2002 | Cline et al. | |
| 2002/0097498 A1 | 7/2002 | Melville et al. | |
| 2002/0139920 A1 | 10/2002 | Seibel et al. | |
| 2002/0148961 A1 * | 10/2002 | Nakasuji et al. | 250/311 |
| 2003/0004412 A1 | 1/2003 | Izatt et al. | |
| 2003/0010825 A1 | 1/2003 | Schmidt et al. | |
| 2003/0010826 A1 | 1/2003 | Dvorkis et al. | |
| 2003/0016187 A1 | 1/2003 | Melville et al. | |
| 2003/0048540 A1 | 3/2003 | Xie et al. | |
| 2003/0082463 A1 * | 5/2003 | Laidig et al. | 430/5 |
| 2003/0142042 A1 | 7/2003 | Tidwell et al. | |
| 2003/0169966 A1 | 9/2003 | Tokizaki | |
| 2003/0202361 A1 | 10/2003 | Johnston et al. | |
| 2003/0234940 A1 * | 12/2003 | Farr et al. | 356/520 |
| 2004/0061072 A1 | 4/2004 | Gu et al. | |
| 2004/0122328 A1 | 6/2004 | Wang et al. | |
| 2004/0153030 A1 | 8/2004 | Novak et al. | |
| 2004/0196213 A1 * | 10/2004 | Tidwell et al. | 345/8 |
| 2004/0212851 A1 | 10/2004 | Osakabe | |
| 2004/0254474 A1 | 12/2004 | Seibel et al. | |
| 2005/0020926 A1 | 1/2005 | Wiklof et al. | |
| 2005/0025368 A1 | 2/2005 | Glukhovsky | |
| 2005/0085708 A1 | 4/2005 | Fauver et al. | |
| 2005/0085721 A1 | 4/2005 | Fauver et al. | |
| 2005/0174610 A1 | 8/2005 | Fukawa | |
| 2005/0182295 A1 | 8/2005 | Soper et al. | |
| 2005/0238277 A1 | 10/2005 | Wang et al. | |
| 2006/0072189 A1 | 4/2006 | DiMarzio | |
| 2006/0072843 A1 * | 4/2006 | Johnston | 382/254 |
| 2006/0072874 A1 | 4/2006 | Johnston | |
| 2006/0077121 A1 | 4/2006 | Melville et al. | |
| 2006/0138238 A1 | 6/2006 | Johnston et al. | |
| 2006/0149134 A1 | 7/2006 | Soper et al. | |
| 2006/0186325 A1 | 8/2006 | Johnston et al. | |
| 2006/0195014 A1 | 8/2006 | Seibel et al. | |
| 2006/0226231 A1 | 10/2006 | Johnston et al. | |
| 2006/0287647 A1 | 12/2006 | Torchia et al. | |
| 2007/0032896 A1 * | 2/2007 | Ye et al. | 700/108 |
| 2007/0057186 A1 * | 3/2007 | Nakasuji et al. | 250/310 |
| 2007/0081168 A1 | 4/2007 | Johnston et al. | |
| 2007/0091426 A1 | 4/2007 | Johnston et al. | |
| 2007/0117030 A1 * | 5/2007 | Laidig et al. | 430/5 |
| 2007/0129601 A1 | 6/2007 | Johnston et al. | |
| 2007/0135693 A1 | 6/2007 | Melman et al. | |
| 2007/0142707 A1 * | 6/2007 | Wiklof et al. | 600/118 |
| 2007/0156021 A1 | 7/2007 | Morse et al. | |
| 2007/0273930 A1 | 11/2007 | Berier et al. | |
| 2008/0144998 A1 | 6/2008 | Melville et al. | |
| 2008/0161648 A1 | 7/2008 | Karasawa | |
| 2010/0142850 A1 * | 6/2010 | Weiner et al. | 382/275 |

FOREIGN PATENT DOCUMENTS

| | | |
|---|---|---|
| EP | 1360927 | 11/2003 |
| EP | 1864606 | 12/2007 |
| GB | 2057709 | 4/1981 |
| GB | 2378259 | 2/2003 |
| JP | 08211313 | 8/1996 |
| WO | WO-9300551 | 1/1993 |
| WO | WO-01/74266 | 10/2001 |
| WO | WO-0174266 | 10/2001 |
| WO | WO-03019661 | 3/2003 |
| WO | WO-2004040267 | 5/2004 |
| WO | WO-2004068218 | 8/2004 |
| WO | WO-2005009513 | 2/2005 |
| WO | WO-2006004743 | 1/2006 |
| WO | WO-2006041452 | 4/2006 |
| WO | WO-2006041459 | 4/2006 |
| WO | WO-2006071216 | 7/2006 |
| WO | WO-2006096155 | 9/2006 |
| WO | WO-2006104489 | 10/2006 |
| WO | WO-2006106853 | 10/2006 |
| WO | WO-2006124800 | 11/2006 |
| WO | WO-2007018494 | 2/2007 |
| WO | WO-2007070831 | 6/2007 |
| WO | WO-2008033168 | 3/2008 |

OTHER PUBLICATIONS

"PCT/US2007/009597 International Search Report", (Mar. 18, 2008), 4 pages.

Brown, Christopher M., et al., "Optomechanical design and fabrication of resonant microscanners for a scanning fiber endoscope", *Optical Engineering*, vol. 45, XP002469237, (Apr. 2006), pp. 1-10.

Smithwick, Y. J., et al., "An error space controller for a resonating fiber scanner: simulation and implementation", *Journal of Dynamic Systems, Measurement and Control*, Fairfiled, N.J., U.S., vol. 128, No. 4, XP009095153, ISSN: 0022-0434, (Dec. 2006), pp. 899-913.

Barhoum, Erek S., et al., "Optical modeling of an ultrathin scanning fiber endoscope, a preliminary study of confocal versus non-confocal detection", *Optics Express*, vol. 13, No. 19, (Sep. 8, 2005), pp. 7548-7562.

Brown, Christopher, et al., "A Novel Design for a Scanning Fiberoptic Endoscope", *Human Interface Technology Laboratory*, University of Washington, Seattle, WA 98195, Presented at SPIE's Regional Meeting on Optoelectronics, Photonics, and Imaging, (Nov. 1-2, 1999), 1 page.

Brown, Christopher M., et al., "Mechanical Design and Analysis for a Scanning Fiber Endoscope", *Proceedings of 2001 ASME Int'l Mechanical Engineering Congress and Exposition*, BED-vol. 51, (Nov. 11-16, 2001), 165-166.

Chen, Tailian, et al., "Experiment of Coalescence of Dual Bubbles on Micro Heaters", *Department of Mechanical Engineering*, University of Florida, Gainesville, FL 32611-6300. USA., Printed from the Internet Aug. 13, 2006, 1-10.

Fauver, Mark, et al., "Microfabrication of fiber optic scanners", (2002) In *Proceedings of Optical Scanning II, SPIE 4773*, pp. 102-110., 9 pages.

Johnston, Richard S., et al., "Scanning fiber endoscope prototype performance", *Optical Fibers and Sensors for Medical Applications II, Proc. SPIE*, vol. 4616. (Oct. 13, 2004), 173-179.

Seibel, Eric J., et al., "A full-color scanning fiber endoscope", *Optical Fibers and Sensors for Medical Diagnosis and Treatment Applications. Ed. I Gannot. Proc. SPIE* vol. 6083, (2006), 9-16.

Seibel, Eric J., et al., "Microfabricated optical fiber with microlens that produces large field-of-view, video rate, optical beam scanning for microendoscopy applications", *Optical Fibers and Sensors for Medical Applications III, Proceedings of SPIE* vol. 4957, (2003), 46-55.

Seibel, Eric J., et al., "Modeling optical fiber dynamics for increased efficiencies in scanning fiber applications", *Optical Fibers and Sensors for Medical Applications V, proceedings of SPIE* vol. 5691, (2005), 42-53.

Seibel, Eric J., et al., "P-37: Optical fiber scanning as a microdisplay source for a wearable low vision aid", *Society for Information Display SID 2002*, Boston, MA, (May 19-24, 2002), 1-4.

Seibel, Eric J., et al., "Prototype scanning fiber endoscope", *Optial Fibers and Sensors for Medical Applications II, Proc. of SPIE*, vol. 4616, (2002), 1-7.

Seibel, Eric J., et al., "Single fiber flexible endocope: general design for small size, high resoljution, and wide field of view", *Human Interface Technology Laboratory*, College of Engineering, University of Washington, Seattle, WA, Proceedings of the SPIE, Biomonitoring and Endoscopy Technologies 4158, 11 pages.

Seibel, Eric J., et al., "Ultrathin laser scanning bronchoscope and guidance system for the peripheral lung", *11th World Conference on Lung Cancer*, (2005), p. 178.

Seibel, Eric J., et al., "Unique Features of Optical Scanning, Single Fiber Endoscopy", *Lasers in Surgery and Medicine 30*, (2002), 177-183.

Seibel, Eric, et al., "Unique Features of Scanning Fiber Optical Endopscopy", *2000 Annual Fall Meeting Abstracts T4.57*, (2000), 1.

Smithwick, Quinn Y., et al., "54.3: Modeling and Control of the Resonant Fiber Scanner for Laser Scanning Display or Acquisition", *Department of Aeronautics and Astronautics*, University of Washington, Seattle, WA SID 03 Digest, (2003), 1455-1457.

Smithwick, Quinn Y., et al., "A Nonlinear State-Space Model of a Resonating Single Fiber Scanner for Tracking Control: Theory and Experiment", *Transactions fo the ASME*, vol. 126, (Mar. 2004), 88-101.

Smithwick, Quinn Y., et al., "Control Aspects of the Single Fiber Scanning Endoscope", (2001) *SPIE Optical Fibers and Sensors for Medical Applications*, 4253, 176-188., 15 pages.

Smithwick, Quinn Y., et al., "Depth Enhancement using a Scanning Fiber Optical Endoscope", *Department of Aeronautics, Human Interface Technology Laboratory*, University of Washington, Seattle, Washington, Optical Biopsy IV, Proc. SPIE 4613, (2002), 12 pages.

Tuttle, Brandon W., et al., "Delivery of therapeutic laser light using a singlemode silica fiber for a scanning fiber endoscope system", *Optical Fibers and Sensors for Medical Diagnostics and Treatment Applications VI, Proc of SPIE* vol. 6083,, (2006), 608307-1 to608307-12.

Wang, Wei-Chih, et al., "Development of an Optical Waveguide Cantilever Scanner", *Opto-Ireland 2002: Optics and Photonics Technologies and Applications, Proceedings of SPIE* vol. 4876 (2003), 72-83.

Wang, Wei-Chih, et al., "Micromachined opital waveguide cantilever as a resonant optical scanner", *Department of Mechanical Engineering*, University of Washington, Seattle, WA 98195, *Sensors and Actuators A 102*, (2002), 165-175.

"PCT/US2007/009598 International Search Report", (Jan. 3, 2008), 3 pages.

\* cited by examiner

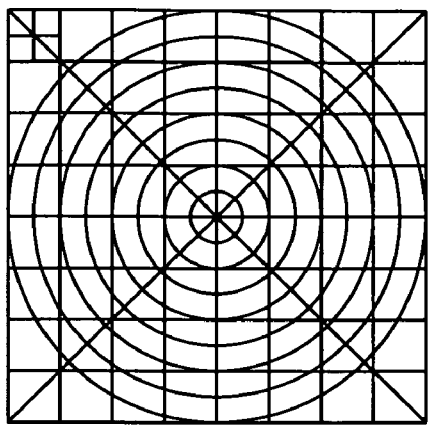
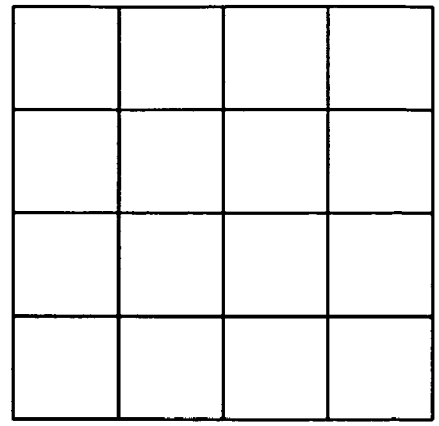
FIG. 10A
FIG. 10B
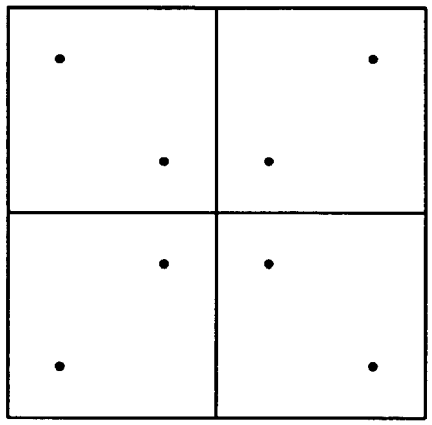
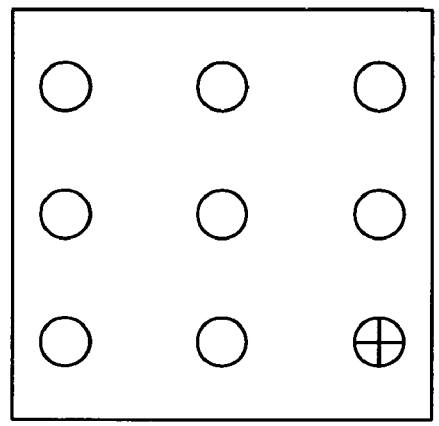
FIG. 10C
FIG. 10D
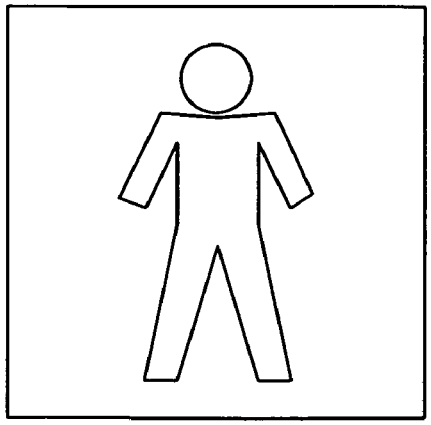
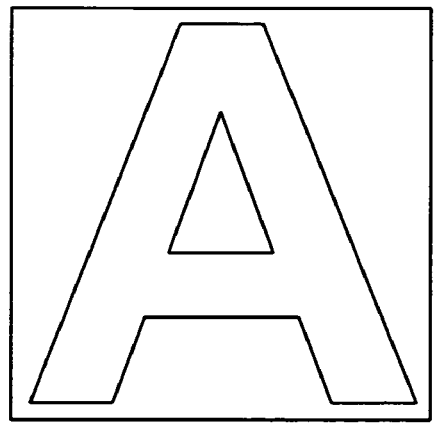
FIG. 10E
FIG. 10F

SCANNING BEAM DEVICE CALIBRATION

BACKGROUND

1. Field

Embodiments of the invention relate to scanning beam devices. In particular, embodiments of the invention relate to calibration of scanning beam devices.

2. Background Information

Various types of scanning beam devices are known in the arts and described in the literature. One type of scanning beam device is a scanning fiber device. The scanning fiber device may include a single, cantilevered optical fiber.

In one aspect, the scanning fiber device may be used to acquire an image of a target area. In acquiring the image of the target area, the single, cantilevered optical fiber may be vibrated in order to scan an illumination spot through an optional lens system and over the target area according to a scan pattern. Backscattered light may be captured, for example by a photosensor, in time series.

In acquiring the image, it generally helps to accurately know the position of the optical fiber and/or the illumination spot throughout the scan. Knowing the drive signal that is used to scan the optical fiber may allow the position of the illumination spot to be estimated for each pixel point in time during the scan pattern. In practice however, environmental variables, manufacturing variables, imperfect electronics, the sensitivity of the scanning fiber device around the resonance frequency, and/or other factors, may tend to limit the accuracy of such estimates. Such positional inaccuracies may also tend to exist in other types of scanning beam devices besides just scanning fiber devices.

If unaccounted for, such positional inaccuracy may tend to add distortion to the image generated using the scanning fiber device.

BRIEF DESCRIPTION OF THE SEVERAL VIEWS OF THE DRAWINGS

The invention may best be understood by referring to the following description and accompanying drawings that are used to illustrate embodiments of the invention. In the drawings:

FIGS. 10A-F are examples of suitable calibration patterns, according to various embodiments of the invention.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

United States Patent Application 20060072843 discloses remapping methods to reduce distortion in images. As disclosed therein, a photosensitive position sensor may be used to actively capture a position of a scanning illumination spot during a scan pattern. However, the use of such a photosensitive position sensor may potentially have certain drawbacks. For one thing, the photosensitive position sensors tend to be expensive. Furthermore, the photosensitive position sensors tend to be limited in size. This may tend to restrict the field of view that may be calibrated. Yet another potential drawback is that the photosensitive position sensors tend to be sensitive to stray or reflected light. This may tend to limit the effectiveness of the calibration. A further potential drawback is that there is one signal path through the photosensitive position sensor during calibration, and a different signal path through a photodetector that is used to detect backscattered light during operation. These different signal paths may have different phase delays, which may tend to complicate calibration and/or add distortion to the images generated. Other drawbacks may also or alternatively be encountered. In any event, methods and apparatus to calibrate a scanning beam device without needing such a photosensitive position sensor may offer certain advantages.

Figure 1:
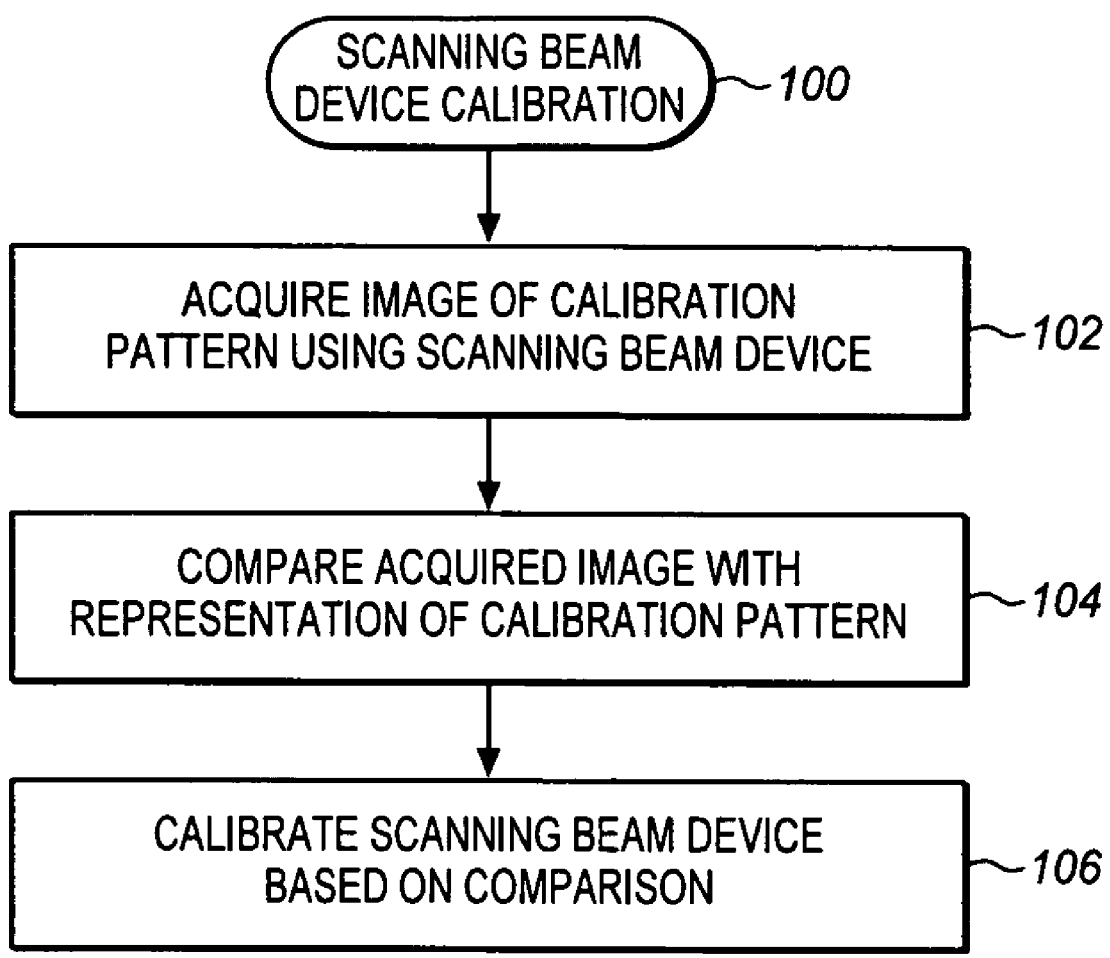
FIG. 1 is a block flow diagram of a method of calibrating a scanning beam device, according to one or more embodiments of the invention.

FIG. 1 is a block flow diagram of a method 100 of calibrating a scanning beam device, according to one or more embodiments of the invention. At block 102, an image of a calibration pattern may be acquired using the scanning beam device. Examples of suitable calibration patterns include, but are not limited to, those shown in FIGS. 10A-F, which will be discussed further below.

Figure 2:
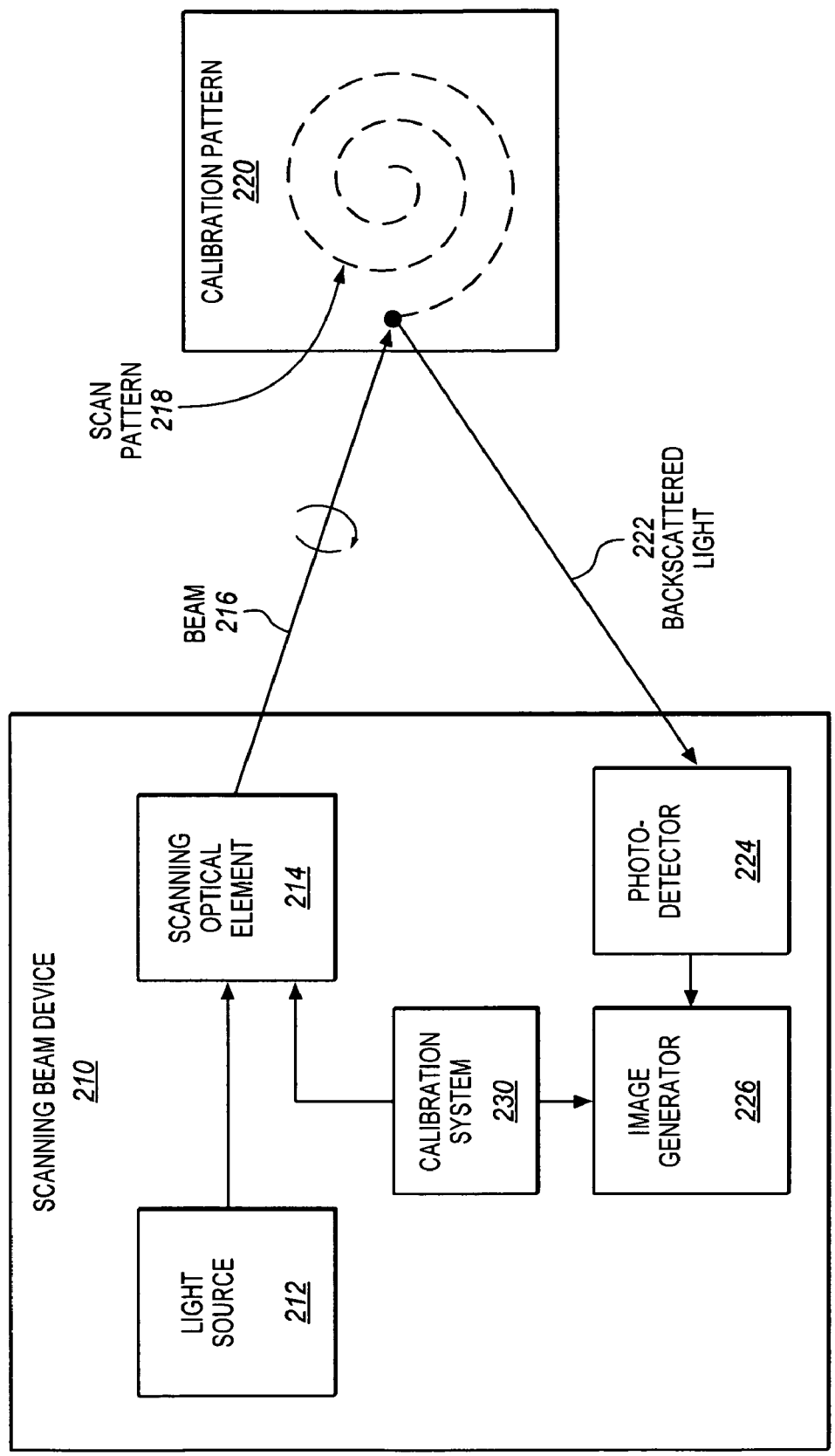
FIG. 2 is a block diagram showing a scanning beam device that is scanning a beam of light over a calibration pattern in a scan pattern, according to one or more embodiments of the invention.

Before discussing the method further, a brief discussion of a scanning beam device and example ways of acquiring an image of a calibration pattern using the scanning beam device may be helpful. FIG. 2 is a block diagram showing a scanning beam device 210 that is scanning a beam of light 216 over a calibration pattern 220 in a scan pattern 218, according to one or more embodiments of the invention. In various embodiments of the invention, the scanning beam device may take the form of an endoscope, scanning fiber endoscope, catheter, bronchoscope, fiberscope, microscope, boroscope, bar code reader, or other image acquisition and/or display device known in the art.

The scanning beam device includes a light source 212. By way of example, the light source may include one or more laser diodes or other lasers. In one aspect, the light source may include one or more of a red light source, a blue light source, a green light source (collectively referred to as an "RGB light source"), a white light source, an infrared light source, an ultraviolet light source, and/or a high intensity laser source (for example for a therapeutic scanning beam device). Depending on the particular implementation, the light source may emit a continuous stream of light, modulated light, or a stream of light pulses. The light source may optionally be configurable to switch between a first mode (for example a continuous stream) and a second mode (for example a stream of light pulses). The light source may optionally include other conventional components, such as, for example, color combiners, filters, and the like.

The light source provides light to a scanning optical element 214. The scanning optical element may include an optical element, such as for example, a waveguide (for example an optical fiber), mirror, or lens. The scanning optical element may also include an actuator, such as, for example, a piezoelectric actuator, a magnetic actuator, an electromagnetic actuator, an electrostatic actuator, a sonic actuator, an electromechanical actuator, other transducer, or other actuator capable of moving the optical element. The actuator may receive electrical signals, which are also referred to herein as a drive signal, and which cause the actuator to move the optical element to scan a beam of light across the calibration pattern in a scan pattern. There is no requirement that the beam be collimated or have parallel rays of light, although it may.

Figure 3:
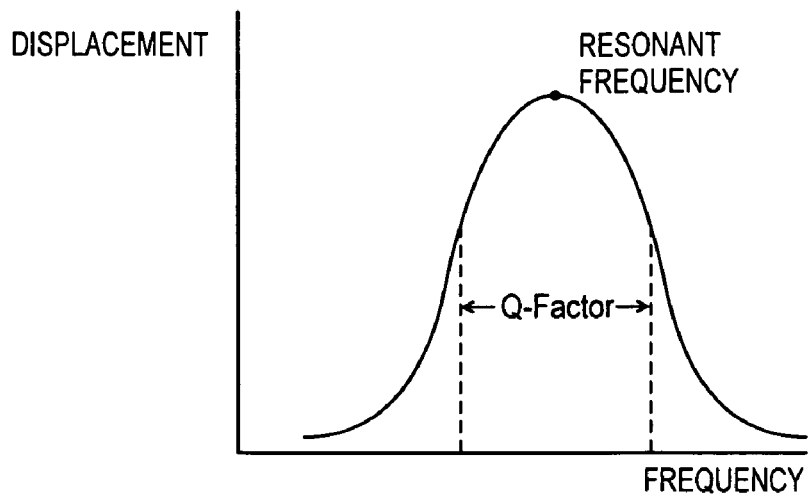
FIG. 3 illustrates scanning an optical element within a Q-factor of its resonance frequency.

While the optical fiber or other scanning optical element may be moved at various frequencies, in one or more embodiments of the invention, the optical fiber or other scanning optical element may be moved within a Q-factor of its mechanical or vibratory resonance frequency (or harmonics of the resonant frequency). This may help to reduce the amount of energy needed to perform the scan. FIG. 3 illustrates scanning an optical element within a Q-factor of its resonance frequency.

In the case of a scanning optical fiber, scanning at or around the resonant frequency, however, may put the illumination spot about 90° out of phase relative to the drive signal. This may tend to make the movement of the optical fiber relatively sensitive to frequency changes immediately around the resonant frequency. For example, if the drive signal is not precisely at resonant frequency, the illumination spot may move from being 90° out of phase to being closer to being in-phase with the drive signal. This may tend to add distortion to the image generated. Similar distortions may potentially be introduced when other scanning optical elements are scanned at or around resonance. As will be explained further below, in one or more embodiments of the invention, pixel position calibration may be used to remove, or at least reduce, distortions due to difficulty in maintaining phase at or around resonance, as well as other distortions that may tend to remain even after drive signal calibration.

Referring again to FIG. 2, as shown, the scan pattern may include a spiral scan pattern, although this is not required. Examples of other suitable scan patterns include, but are not limited to, other radial scan patterns, such as ovals, circles, propeller patterns, and combinations thereof, and non-radial scan patters, such as raster scan patterns, Lissajous scan patterns, and combinations thereof. The scan patterns may be one-dimensional or two-dimensional.

As previously discussed, it generally helps to accurately know the position of the illumination spot or beam throughout the scan. Knowing the drive signal may allow the position of the illumination spot or beam to be estimated for each pixel point in time during the scan pattern. In practice however, environmental variables, manufacturing variables, imperfect electronics, potentially the sensitivity of the scanning beam device around the resonance frequency, and/or other factors, may tend to limit the accuracy of such estimates. Accordingly, the actual positions of the illumination spot throughout the scan may differ from the expected positions. If unaccounted for, such positional differences may tend to add distortion to the image generated using the scanning beam device.

Figure 4:
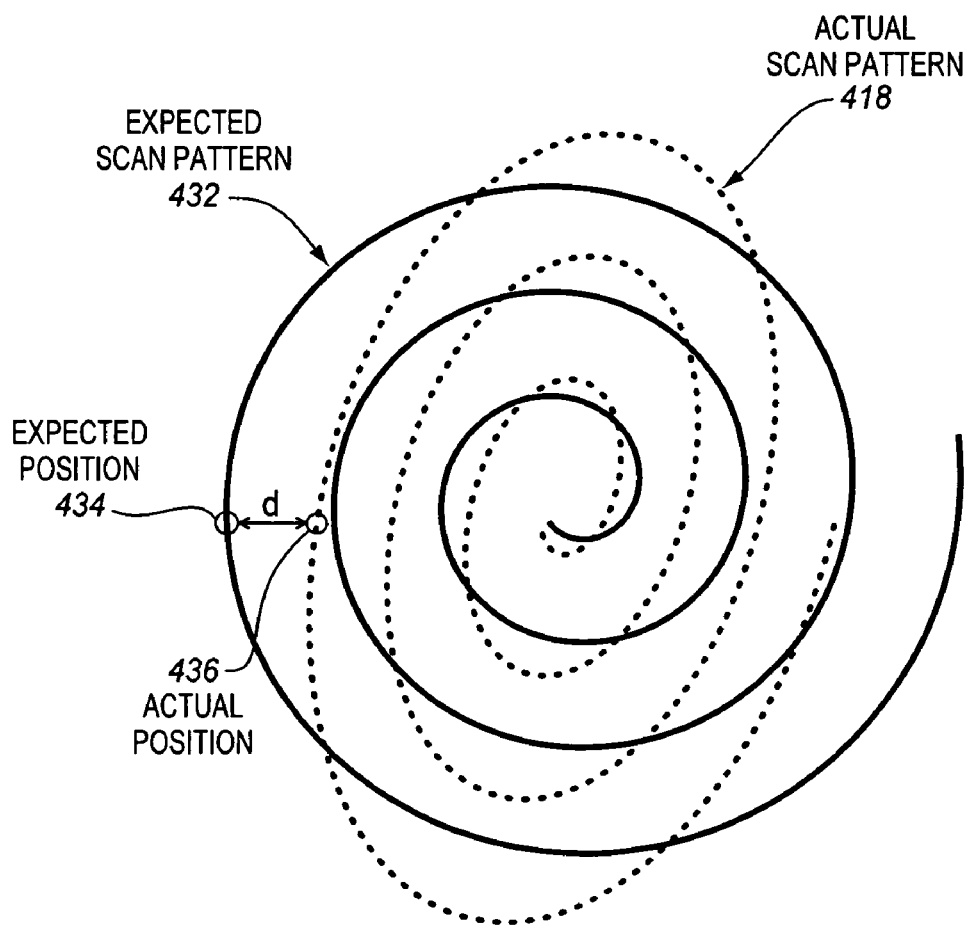
FIG. 4 shows one illustrative example of how an actual or observed scan pattern (shown in dashed lines) may differ from an expected or ideal scan pattern (shown in solid lines), according to one or more embodiments of the invention.

FIG. 4 shows one illustrative example of how an actual or observed scan pattern 418 (shown in dashed lines) may differ from an expected or ideal scan pattern 432 (shown in solid lines), according to one or more embodiments of the invention. In this example, the expected scan pattern follows a circular spiral, whereas the actual scan pattern follows an elliptical spiral. In other implementations, the actual and expected scan patterns may differ in other ways. As shown, the expected positions of the beam throughout the scan may differ significantly from the actual positions of the beam at the corresponding times. A representative distance, d, is used to illustrate a difference between an expected position 434 of the beam and the actual position 436 of the beam at a particular time.

Referring again to FIG. 2, light 222 may be reflected or backscattered from the calibration pattern throughout the scan pattern. The amount of light backscattered may depend in part upon the optical characteristics (for example color, saturation, etc.) of the portion of the calibration pattern that is illuminated by the beam of light at that particular time. Notice that the backscattered light represents the optical characteristics of the calibration pattern at the actual positions of the beam throughout the scan, not the expected positions of the beam.

The scanning beam device includes a photodetector 224. Examples of suitable photodetectors include, but are not limited to, photodiodes, charge coupled devices, photomultiplier tubes, phototransistors, and other photodetectors known in the arts, and combinations thereof. The photodetector may detect the backscattered light at different times throughout the scan pattern. In one or more embodiments of the invention, the photodetector may be located at a distal tip of the scanning beam device (for example in a probe portion) in close proximity to the calibration pattern. Alternatively, in one or more embodiments of the invention, an optical waveguide may be used to convey backscattered light to a photodetector located away from the distal tip (for example in a base station).

The scanning beam device includes an image generator 226 that is coupled with, or otherwise in communication with, the photodetector. The image generator may receive signals representing the amount of light detected at different times throughout the scan pattern. The image generator may use these signals to generate a corresponding image of the calibration pattern. In one or more embodiments of the invention, the image generator may place or represent the backscattered light detected at different times throughout the scan pattern at the expected positions of the beam for those respective times. For ease of description, the backscattered light may be said to be "placed" at a position in the generated image. This is intended to encompass the possibility that the backscattered light is detected, and that an electrical signal "representing"

the amount of detected light is used to represent the backscattered light at the position in the generated image.

Figure 5:
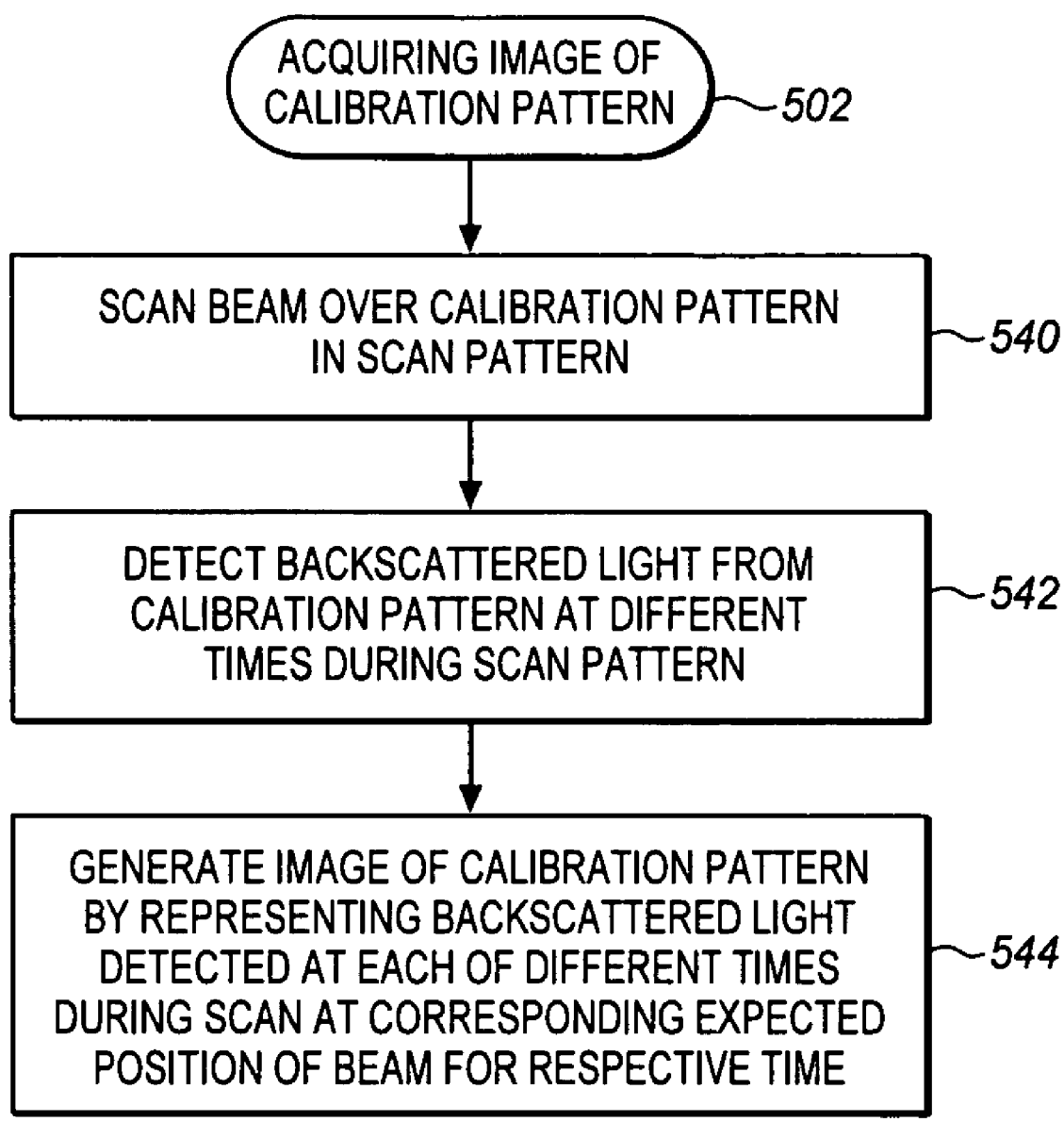
FIG. 5 is a block flow diagram of an exemplary method of acquiring an image of a calibration pattern using a scanning beam device, according to one or more embodiments of the invention.

To briefly review, FIG. 5 is a block flow diagram of an exemplary method 502 of acquiring an image of a calibration pattern using a scanning beam device, according to one or more embodiments of the invention. At block 540, a beam of light may be scanned over the calibration pattern in a scan pattern. Then, light or a portion of the beam backscattered from the calibration pattern may be detected at different times during the scan pattern, at block 542. Then, an image of the calibration pattern may be generated by placing or representing the backscattered light detected at each of the different times at a corresponding expected or ideal position of the beam for a respective time, at block 544. The generated image may also be referred to herein as an acquired image.

As previously mentioned, prior to calibration, the actual positions of the beam may potentially differ from the expected positions of the beam. Placing or representing the backscattered light at the expected positions of the beam may accordingly introduce distortions into the acquired image. If the same drive signal and physical system is used to drive the scanning beam device, these distortions may tend to repeat for each scan (as long as the relevant environmental factors remain constant). These distortions in the acquired image of the calibration pattern may advantageously be used to calibrate the scanning beam device to account for differences between the expected and actual scan patterns, so that the distortions are removed, or at least reduced, in the next image generated using the scanning beam device.

Referring again to FIG. 1, after acquiring the image of the calibration pattern, the acquired image may be compared with a representation of the calibration pattern, at block 104. The representation of the calibration pattern may be a true representation, or at least a more accurate representation of the calibration pattern than the acquired image. As such, a comparison of the distorted acquired image of the calibration pattern with the more accurate representation of the calibration pattern may be used as a metric or guide for calibrating the scanning beam device. In various embodiments, the comparison may be performed manually by a practitioner, automatically by an algorithm, or partly by a practitioner and partly by an algorithm.

Different types of representations of the calibration pattern are possible. In one or more embodiments, the representation may include an electronic image or other electronic likenesses of the calibration pattern. As another option, in one or more embodiments, the representation may include a mental image, picture, impression, or other mental representation of the calibration pattern. As yet another option, in one or more embodiments, the representation may include one or more or a set of features or characteristics of the calibration pattern. For example, the representation may include the number of objects in the calibration pattern, the shapes of the objects, the sizes of objects, the orientations of objects, the colors of objects, or a combination of such features or characteristics. Combinations of such representations are also suitable.

At block 106, the scanning beam device may be calibrated based, at least in part, on the comparison. In one or more embodiments of the invention, calibrating the scanning beam device may include adjusting one or more drive parameters or a drive signal that is used to drive the scanning optical element. By way of example, the adjustment may be used to make the actual scan pattern more closely match the expected scan pattern.

As another option, in one or more embodiments of the invention, calibrating the scanning beam device may include determining and potentially storing or otherwise preserving calibrated image position information (for example calibrated destination pixels for different times in the scan). The calibrated image position information may be based on differences between the acquired image and the representation, which in turn may be based on differences between the actual and expected scan patterns. By way of example, the calibrated image position information may be used to adjust the placement in a subsequently generated image of backscattered light detected at different times during the scan pattern in order to account for differences between the actual and expected scan patterns for the present drive signal and/or reduce distortion.

As yet another option, in one or more embodiments of the invention, a combination of both drive signal calibration and pixel position calibration may optionally be performed. Typically, one or more or quite a few drive signal calibrations may be performed, and then one or more pixel position calibrations may subsequently be performed.

Figure 6:
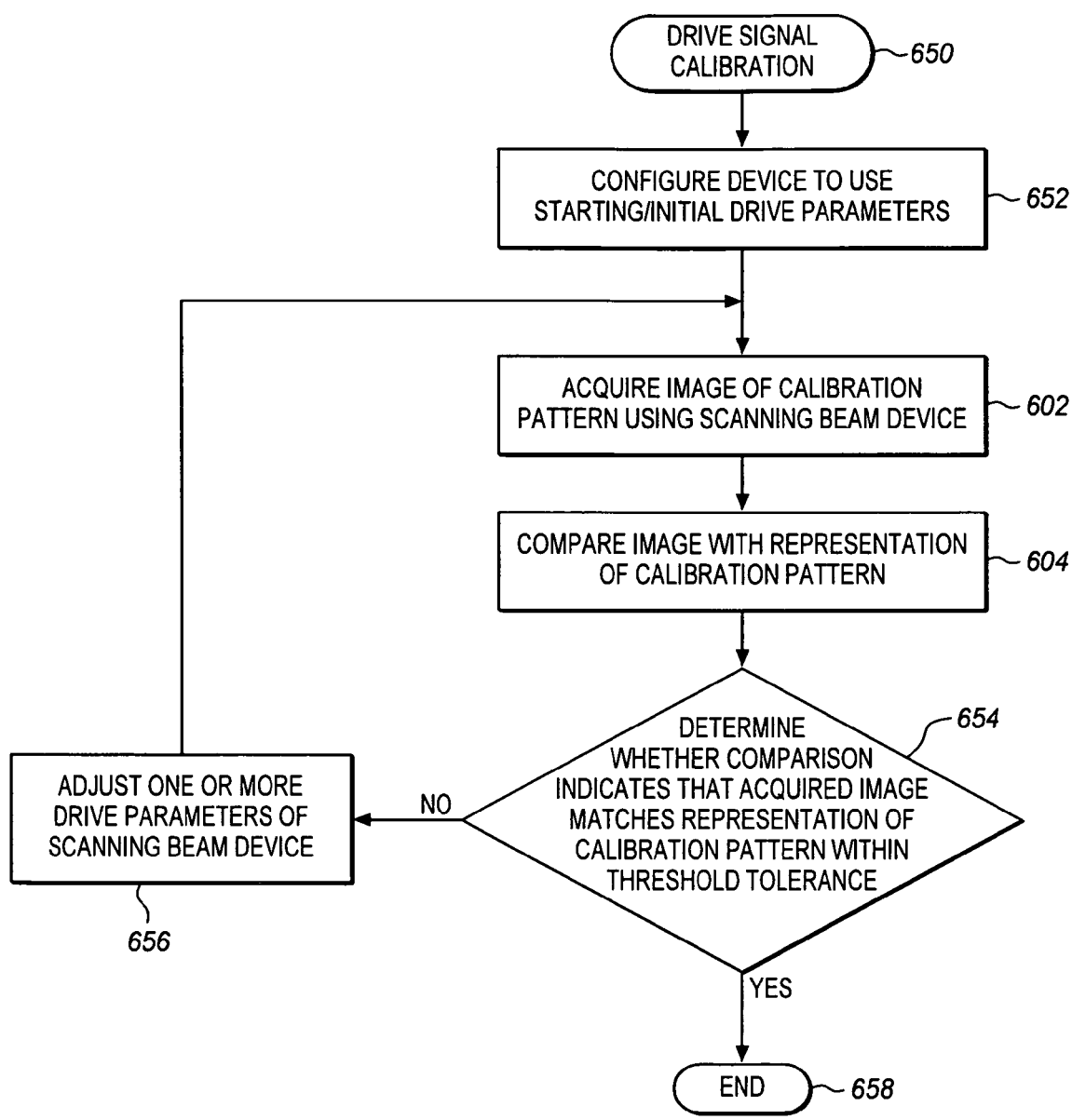
FIG. 6 is a block flow diagram of a method of drive signal calibration, according to one or more embodiments of the invention.

FIG. 6 is a block flow diagram of a method 650 of drive signal calibration, according to one or more embodiments of the invention. At block 652, the scanning beam device may be configured to use a set of starting or initial drive parameters. The initial drive parameters may be estimated, determined theoretically, or otherwise determined. As one option, the initial drive parameters may be stored in and accessed from a memory. For example, suitable configuration memories are disclosed in U.S. Patent Application 20060072874, filed Apr. 6, 2006. As another option, a compact disc or other machine-readable medium having the initial drive parameters stored thereon may be shipped with the scanning beam device. As yet another option, the initial drive parameters may be accessed over the Internet or another network. As a still further option, a practitioner may manually enter or set the initial drive parameters, which may optionally be provided in a set of instructions for use. Alternatively, the scanning beam device may be configured to use the initial drive parameters using other approaches known in the arts.

The particular drive parameters depend upon the type of scanning beam device and the scan pattern. By way of example, representative drive parameters for a scanning fiber device that is to be scanned in a spiral scan pattern include: (1) a maximum x-axis drive voltage; (2) a maximum y-axis drive voltage; (3) a phase difference between the x-axis and y-axis drive voltages; (4) a slope of a voltage ramp/increase; and (5) optionally a change in the slope of the voltage ramp/increase. The height and width of the spiral tend to be directly related to the y-axis and x-axis drive voltages, respectively. The rate of increase of the spiral cross-section tends to be directly related to the slope of the voltage ramp/increase. A change in the slope of the voltage ramp/increase, which is optional, may be used to achieve more uniform rate of increase of the spiral diameter over the scan.

At block 602, an image of a calibration pattern may be acquired using the scanning beam device. The image may be acquired by scanning the beam over the calibration pattern in the scan pattern using the starting or initial drive parameters. Then, the acquired image may be compared with a representation of the calibration pattern, at block 604. These operations may be performed substantially as previously described.

At block 654, a determination may be made whether the comparison indicates that the acquired image matches the representation of the calibration pattern within a threshold tolerance. Different ways of making this determination are possible and have been done.

As one option, in one or more embodiments of the invention, this determination may include comparing sizes and/or shapes of objects in the acquired image and the representation of the calibration pattern and determining whether they match within the threshold tolerance. As one example, a radius or average radius of a circle in the acquired image may be compared with a radius or average radius of the circle in the representation and determining if they match within a threshold tolerance. As another example, the degree of circularity of a circle in the acquired image may be tested, for example, by taking a ratio of a maximum radius of the circle to a minimum radius of the circle and determining if the ratio differs from one by less than a threshold tolerance. Alternatively, other sizes and/or shapes of other objects may be compared.

As another option, in one or more embodiments of the invention, this determination may include comparing a position of a point in the acquired image with a position of the corresponding point in the representation of the calibration pattern, and determining if the positions differ by less than a threshold distance or tolerance. The point may be a fixed point, a point chosen at random, or a point chosen according to a schedule, for example. Squared or absolute values of distances may also optionally be used. If desired, multiple corresponding pairs of points potentially spread throughout the pattern may optionally be used.

As yet another option, in one or more embodiments of the invention, the comparison of the acquired image with the representation of the calibration pattern may include inferring or estimating actual coordinates of the scanned beam at different times during the scan. The acquired image of the calibration pattern may be examined and one or more points or other features thereof may be identified. For example, the top, bottom, right, and left of one of the circles shown in FIG. 10A may be identified. Then, one or more corresponding features may be identified in the representation of the calibration pattern. The coordinates, such as, for example, the x,y-coordinates or the polar coordinates, of each of the one or more features in the representation of the calibration pattern may be known and may be identified. By way of example, the representation of the calibration pattern may have an associated coordinate system in which the one or more points or other features may have implicit coordinates. Then, the coordinates of a given feature in the acquired image may be assumed to be the same as the known coordinates of the given feature in the representation of the calibration pattern. In this way, points or other features in the acquired image may be mapped to known coordinates of corresponding points or other features in the representation of the calibration pattern. These coordinates may serve as estimates of the actual position of the scanning beam at different times during the scan pattern, and may be used for calibration as described further below.

These are just a few illustrative examples. Combinations of these example approaches may also optionally be used. Other methods of statistical, empirical, or heuristic pattern comparison will be apparent to those skilled in the arts, and having the benefit of the present disclosure.

If the acquired image does not sufficiently match the representation of the calibration pattern (i.e., "no" is the determination), then the method may advance from block 654 to block 656. At block 656, one or more drive parameters of the scanning beam device may be adjusted. The adjustment of the one or more drive parameters may advantageously help to make a subsequently acquired image of the calibration pattern more closely match the representation of the calibration pattern.

Different ways of adjusting the drive parameters are possible. In one or more embodiments of the invention, a practitioner may manually adjust the parameters. If desired, the practitioner may perform calculations, or use simulations or other models of the scanning beam device in order to help guide the adjustments. As another option, the practitioner may adjust the parameters based on experience, intuition, or relatively randomly. As another option, in one or more embodiments of the invention, a control loop may be used to adjust the parameters. The control loop may be implemented in hardware, software, or a combination of hardware and software. In various aspects, the control loop may adjust the parameters based on calculations, or a simulation or model of the operation of the scanning beam device, or using an intelligent search or optimization method. Alternatively, the control loop may adjust the parameters relatively empirically (for example using a Monte Carlo method). These are just a few examples. Other approaches will be apparent to those skilled in the art, and having the benefit of the present disclosure.

The particular way in which the drive parameters are adjusted may depend upon the type of scanning beam device and the scan pattern. By way of example, consider some possible adjustments to the drive parameters of a scanning fiber device operated in a spiral scan pattern.

As one example, the comparison may indicate that the zoom or magnitude of the scan is off. For example, only a portion of an object or a subset of the objects in a calibration pattern may appear in the acquired image. This distortion may be reduced by adjusting the slopes of both the x-axis and y-axis voltage ramp/increase. The maximum drive voltages may be increased to expand a spiral or decreased to compress a spiral. If desired, a change in the slopes of the x-axis and y-axis voltage ramp/increase (e.g., a change in the maximum drive voltages) may be used to help achieve a more uniform rate of increase of the spiral diameter over the scan.

As another example, the comparison may indicate that the spiral scan pattern is elliptical, such as, for example, as shown in FIG. 4. In such a case, a y-axis drive voltage may be reduced relative to an x-axis drive voltage in order to make a vertically elliptical spiral scan pattern more circular. Alternatively, an x-axis drive voltage may be reduced relative to a y-axis drive voltage in order to make a horizontally elliptical spiral scan pattern more circular.

As yet another example, in one or more embodiments of the invention, estimates of the actual coordinates of the scanned beam at different times during the scan may be available through mapping features in the acquired image to known coordinates of corresponding features in the representation of the calibration pattern. In such a case, the estimated actual coordinates may be used to guide in calibration. To further illustrate, in the case of a practitioner performing the adjustment, the estimated actual coordinates and the expected/ideal coordinates of the scanned beam may be plotted at different times during the scan. For example, a plot similar to that shown in FIG. 4 may be generated. The plot, which is optional, may help a practitioner to see the differences and to see the drive signal adjustments that would reduce the differences. By way of example, if as shown in FIG. 4 the maximum y-value of the actual scan pattern is greater than the maximum y-value of the expected scan pattern, then the maximum y-axis drive voltage may be reduced to vertically compress the scan. Similarly, if as shown in FIG. 4 the maximum x-value of the actual scan pattern is less than the maximum x-value of the expected scan pattern, then the maximum x-axis drive voltage may be increased to horizontally expand the scan. These adjustments may help to circularize the elliptical scan. Another potential advantage of knowing the coordinates is that amounts of the adjustment may be mathematically calculated using, for example, ratios of coordinates or distances associated with the coordinates, etc. An algorithm may similarly make such adjustments using the coordinates but potentially without the making of such plots.

These are just a few illustrative examples. Other examples will be apparent to those skilled in the art and having the benefit of the present disclosure.

After adjusting the one or more drive parameters, at block 656, the method may revisit blocks 602, 604, and 654 one or more times. In some cases, the method may loop through blocks 602, 604, 654, and 656 anywhere from several times up to a hundred times, or more if desired. At least to a point, more loops may tend to promote better calibration of the drive signal of the scanning beam device. At some point, if and when the acquired image sufficiently matches the representation of the calibration pattern (i.e., "yes" is the determination at block 654), then the method may advance from block 654 to block 658. Alternatively, other criteria may optionally be used, such as, for example, if a given number of iterations of the method have been performed.

At block 658, the drive signal calibration method may "end". The adjusted parameters may be stored or otherwise preserved in place of the starting/initial drive parameters. In one or more embodiments, the adjusted drive parameters may optionally be stored in the aforementioned configuration memory described in United States Patent Application 20060072843. The adjusted drive parameters may be used by the drive electronics when the device is next operated, such as, for example, for further calibration or for its intended purpose of use.

A particular method 650 has been shown and described to illustrate certain concepts, although the scope of the invention is not limited to this particular method. In alternate embodiments, operations may optionally be omitted from and/or added to the method. For example, the determination at block 654 may optionally be omitted. Rather than making such a determination, a given number of one or more iterations of the method may optionally be performed, with the number optionally being configurable. As another example, an adjustment and/or an amount of an adjustment may optionally be calculated between blocks 604 and 656. The calculated adjustment may optionally be based on a simulation, computer model, or optimization model, and may tend to help obtain rapid drive signal calibration. Other modifications and/or adaptations are also possible and will be apparent to those skilled in the art and having the benefit of the present disclosure.

Figure 7:
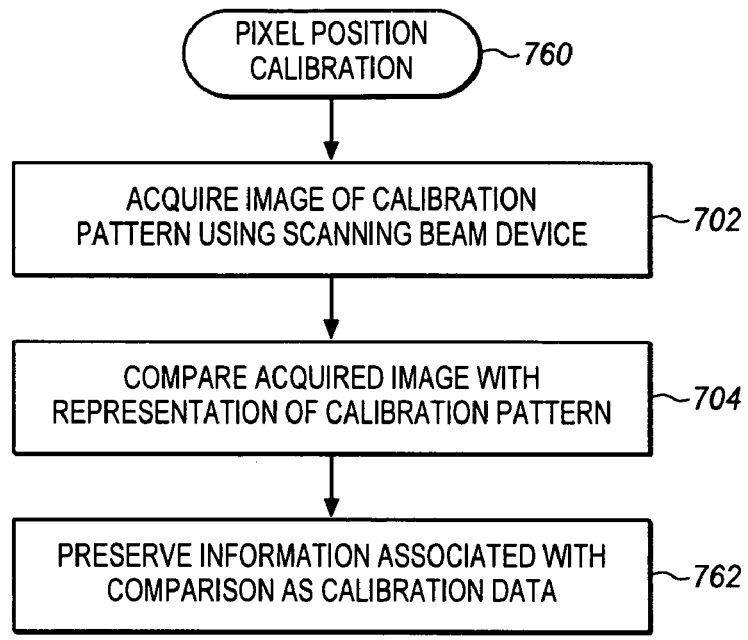
FIG. 7 is a block flow diagram of a method of pixel position calibration, according to one or more embodiments of the invention.

FIG. 7 is a block flow diagram of a method 760 of pixel position calibration, according to one or more embodiments of the invention. At block 702, an image of a calibration pattern may be acquired using the scanning beam device. This may be performed substantially as previously described. If drive signal calibration has been previously performed, then the image may be acquired by scanning the beam over the calibration pattern in the scan pattern using the adjusted drive parameters. Either the same calibration pattern as used for the drive signal calibration, or a different calibration pattern entirely (potentially better suited for pixel position calibration), may be used. Alternatively, if no drive signal calibration has been performed, then starting/initial drive parameters may be used.

Then, the acquired image may be compared with a representation of the calibration pattern, at block 704. The comparison may be performed substantially as previously described.

At block 762, calibrated image position information associated with the comparison may be determined and stored (for example in a memory of the scanning beam device) or otherwise preserved. In one or more embodiments of the invention, the calibration data may be stored in the aforementioned configuration memory described in United States Patent Application 20060072843, although this is not required.

In one or more embodiments of the invention, the calibrated image position information may include calibrated destination pixel positions for respective time points during a scan. The calibrated destination pixel positions may attempt to represent or estimate the actual positions of the beam rather than the expected positions of the beam as inferred indirectly by differences between the acquired image and representation of the calibration pattern and/or by mapping points or features of the acquired image to corresponding known coordinates in the representation of the calibration pattern. As another option, in one or more embodiments of the invention, the information may include directional offsets or displacements, for example, from the expected positions of the beam. As yet another option, the information may include a combination of both destination pixel positions and offsets or displacements. Advantageously, such pixel position calibration may help to remove, or at least reduce, distortions due to operating at or around a mechanical resonance frequency, or other distortions that may tend to remain after drive signal calibration.

A particular method 760 has been shown and described to illustrate certain concepts, although the scope of the invention is not limited to this particular method. In alternate embodiments, operations may optionally be added to the method. For example, the method may optionally be repeated one or more times to fine-tune the calibrated image pixel or other position information. As another example, multiple images may be acquired and compared to statistically average the calibration data that is preserved. Other modifications and/or adaptations are also possible and will be apparent to those skilled in the art and having the benefit of the present disclosure.

The scanning beam device may be used to generate black and white images, color images, or both. Different ways of calibrating the scanning beam device to generate color images are possible.

One way of calibrating the scanning beam device to generate color images, in accordance with one or more embodiments of the invention, involves using a black and white calibration pattern. Different images of the black and white calibration pattern may be acquired by scanning beams of differently colored lights over the black and white calibration pattern. In one or more embodiments, the differently colored lights may include red, green, and blue lights, although the scope of the invention is not so limited. Backscattered light for each of the differently colored lights may be detected. The black portions of the pattern may tend to absorb most of the light of each of the different colors, while the white portions may tend to reflect most of the light of each of the different colors.

Each of the different acquired images may be compared with the representation of the black and white calibration pattern. In some cases, such as, for example, if chromatic aberration is present (the lens may tend to add chromatic aberration), each of the different colors may differ from the representation differently. Accordingly, in one or more embodiments of the invention, the scanning beam device may be calibrated by different amounts for each of the different colored lights. This may help to reduce the visual affects of chromatic aberration, if present.

Different ways of preserving the calibration data for the differently colored lights are possible. In one or more embodiments of the invention, different destination pixel positions for each of a plurality of times during the scan may be stored for each of the differently colored lights. As another option, in one or more embodiments of the invention, destination pixel positions for each of a plurality of times during the scan may be stored for one of the colored lights (e.g., the red light), and potentially different offsets from these stored destination pixel positions may be stored for each of the times for the remaining differently colored lights (e.g., the green and blue lights).

Another way of calibrating the scanning beam device to generate color images, in accordance with one or more embodiments of the invention, involves using a multi-colored calibration pattern. Different images of the multi-colored calibration pattern may be acquired by scanning multi-colored light (e.g., white light) over the multi-colored calibration pattern, separating the backscattered light into color components, and detecting the color components. Then, each of the different color component images may be compared with the corresponding color component of the calibration pattern. The calibration data for the differently colored lights may be preserved as described in the previous paragraph, or otherwise.

Figure 8:
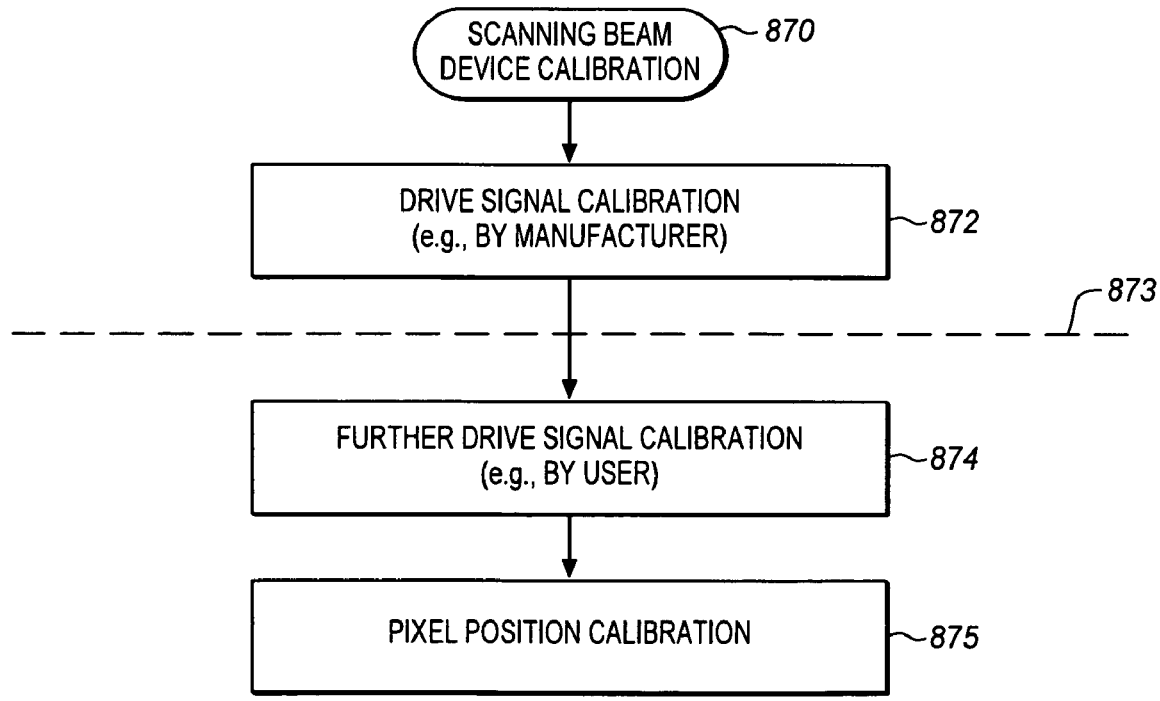
FIG. 8 is a block flow diagram of one particular example of a method of scanning beam device calibration, according to one or more embodiments of the invention.

The calibrations as described herein may potentially be performed at different times, and potentially by different entities. FIG. 8 is a block flow diagram of one particular example of a method 870 of scanning beam device calibration, according to one or more embodiments of the invention.

At block 872, drive signal calibration as described herein may be performed. In one or more embodiments of the invention, a manufacturer or other first entity may perform the drive signal calibration of block 872. Then, the partially calibrated scanning beam device may be sold, given, or otherwise transferred to a purchaser, user, or other second entity. At block 874, further drive signal calibration as described herein may optionally be performed. This may help to customize the scanning beam device to a particular use environment, such as, for example, a particular drive system, since the systems used to drive the scanning beam device in the manufacturing and use environments may potentially differ. Then, at block 875, pixel position calibration as described herein may be performed. A dashed line 873 is used to show that a portion of the calibration of the scanning beam device may be performed by a first entity, such as, for example, a device manufacturer, and a second portion of the calibration may be performed by a second entity, such as, for example, a purchaser and/or user.

Alternate embodiments are also possible. As one example, the second entity may perform pixel position calibration without performing further drive signal calibration. As another example, the first entity may perform pixel position calibration after performing drive signal calibration, and the second entity may perform further drive signal calibration and/or pixel position calibration. Furthermore, it is to be appreciated that various types of calibration as disclosed herein may be performed at other times, such as, for example, when distortions are detected or become significant, when new equipment is to be used, according to regularly scheduled maintenance, or according to other known criteria.

Figure 9:
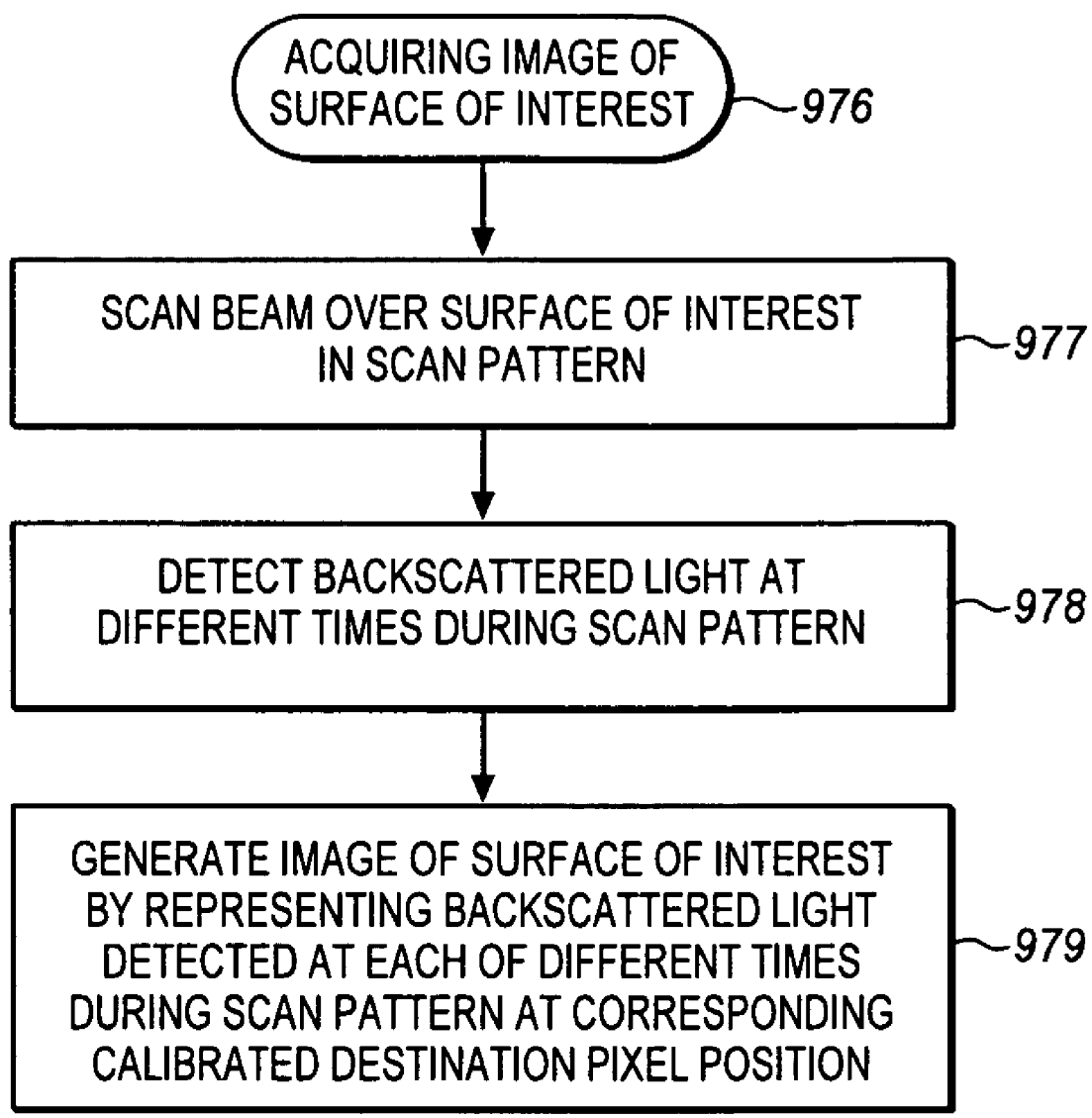
FIG. 9 is a block flow diagram of a method of acquiring an image of a surface of interest, according to one or more embodiments of the invention.

FIG. 9 is a block flow diagram of a method 976 of acquiring an image of a surface of interest, according to one or more embodiments of the invention. In one or more embodiments of the invention, for example if the scanning beam device is an endoscope or other medical device to be inserted into a patient, the scanning beam device may be advanced through the body and positioned adjacent a target surface, such as, for example, a body tissue, body lumen, body cavity, hollow organ, or like surfaces of interest, and then an image of the target surface may be acquired. However, the scope of the invention is not limited to such surfaces, since other surfaces such as bar codes and other surfaces are also suitable.

At block 977, a beam may be scanned over the surface of interest in a scan pattern. In one or more embodiments, calibrated drive parameters determined as described herein may be used. Alternatively, starting or initial drive parameters may be used. Backscattered light may be detected at different times during the scan pattern, at block 978. Then, at block 979, an image of the surface of interest may be generated. In one or more embodiments of the invention, generating the image may include placing or representing backscattered light detected at each of a plurality of different times during the scan pattern at a corresponding calibrated destination image position in the generated image. As previously mentioned, in one or more embodiments of the invention, the calibrated destination image position may include destination pixel positions for respective time points during a scan. As another option, offsets or displacements may also or alternatively be used. The destination pixel positions and/or offsets may attempt to represent the actual positions of the beam rather than the expected positions of the beam as inferred indirectly by differences between the acquired image and representation of the calibration pattern.

An analogous embodiment is also possible for displaying an image. The calibrated drive parameters determined as described herein may be used during the scan. Modulated light may be placed or represented at the calibrated image positions determined as described herein.

FIGS. 10A-F are examples of suitable calibration patterns, according to various embodiments of the invention. FIG. 10A is a calibration pattern including a grid of equally spaced horizontal and vertical lines, eight concentric circles of constantly increasing diameter, diagonal lines intersecting at the center of the concentric circles, and a reference, plus sign in the upper left corner.

FIG. 10B is a calibration pattern that consists of grid of equally spaced horizontal and vertical lines. Various other calibration patterns including angled grids or grids with different spacings are also possible.

FIG. 10C is a calibration pattern that consists of a pair of central, intersecting, horizontal and vertical lines, and eight points. The eight points lie along pattern diagonals, with two points in each of four quadrants. Various other calibration patterns are possible to include different numbers and arrangements of points and lines.

FIG. 10D is a calibration pattern that consists of a regular matrix of nine small circles of the same size with one of the circles having a distinguishing mark such as a cross therein. Attributes that may be used for calibration include the number and size of the circles in the acquired image. The distinguishably marked circle may provide an orientation.

FIG. 10E is a calibration pattern that consists of a stick figure of a person. A wide variety of other calibration patterns may include simple drawings of animals, objects, scenes, and a wide variety of other subjects.

FIG. 10F is a calibration pattern that consists of the letter A in outline form. Other letters, numbers, and combinations thereof potentially with other objects, are also suitable.

These particular calibration patterns are merely illustrative. Other suitable calibration patterns may include a wide variety of different patterns, ranging from abstract groups of points or lines, to geometric shapes, to non-geometric shapes, to objects, to pictograms, to images, photographs, art, and combinations of such patterns. Almost any pattern that may be used to perform one or more of the calibrations disclosed herein may be used. The term "calibration pattern" is accordingly to be interpreted broadly.

To further illustrate certain concepts, consider several example ways in which the calibration pattern shown in FIG. 10A may be used for calibration. This calibration pattern has various predetermined features or characteristics that may be compared to the acquired image and used for calibration.

One characteristic is the number of circles. The calibration pattern has eight concentric circles. If fewer than eight circles appear in the acquired image, then, by way of example, the drive signal (for example the x-axis and y-axis voltages) may be adjusted to adjust the magnitude of the scan.

Another characteristic is the size of the circles. By way of example, if all of the circles are smaller in the acquired image than in the calibration pattern, then the drive signal may be adjusted to adjust the magnitude of the scan. Alternatively, if the larger, outer circles are the right size, but the smaller, inner circles are too small, a change in the voltage ramp/increase may be used to promote more even rate of increase of spiral diameter.

Yet another characteristic is the shape of the circles. In some cases the circles may be elliptical. One potential metric for lack of circularity is deviation of the ratio of the maximum and minimum radiuses from unity (the number one). One way of determining how round the circle is may involve assessing the deviation of the ratio of the maximum and minimum radiuses of the circle from unity. If the circles appear as horizontal ellipses in the acquired image, then the y-axis voltage may be decreased relative to the x-axis voltage. Alternatively, if the circles appear as vertical ellipses in the acquired image, then the x-axis voltage may be decreased relative to the y-axis voltage.

Similarly, a further characteristic is the equal spacing of the horizontal and vertical lines. If the spacing between the horizontal lines is greater than the spacing between the vertical lines in the acquired image, this may potentially indicate a vertical elliptical scan pattern as opposed to a truly circular scan pattern. In such case, by way of example, the y-axis voltage may be decreased relative to the x-axis voltage.

These provide a few illustrative ways in which the comparison of the acquired image with the representation may be used to adjust drive parameters. Numerous other ways are also possible and have also been used. Those skilled in the art and having the benefit of the present disclosure will appreciate that there is a great deal of flexibility in the different types of calibration patterns that may be used and in the associated different comparisons of the features of the calibration patterns that may be used to make adjustments.

Figure 11:
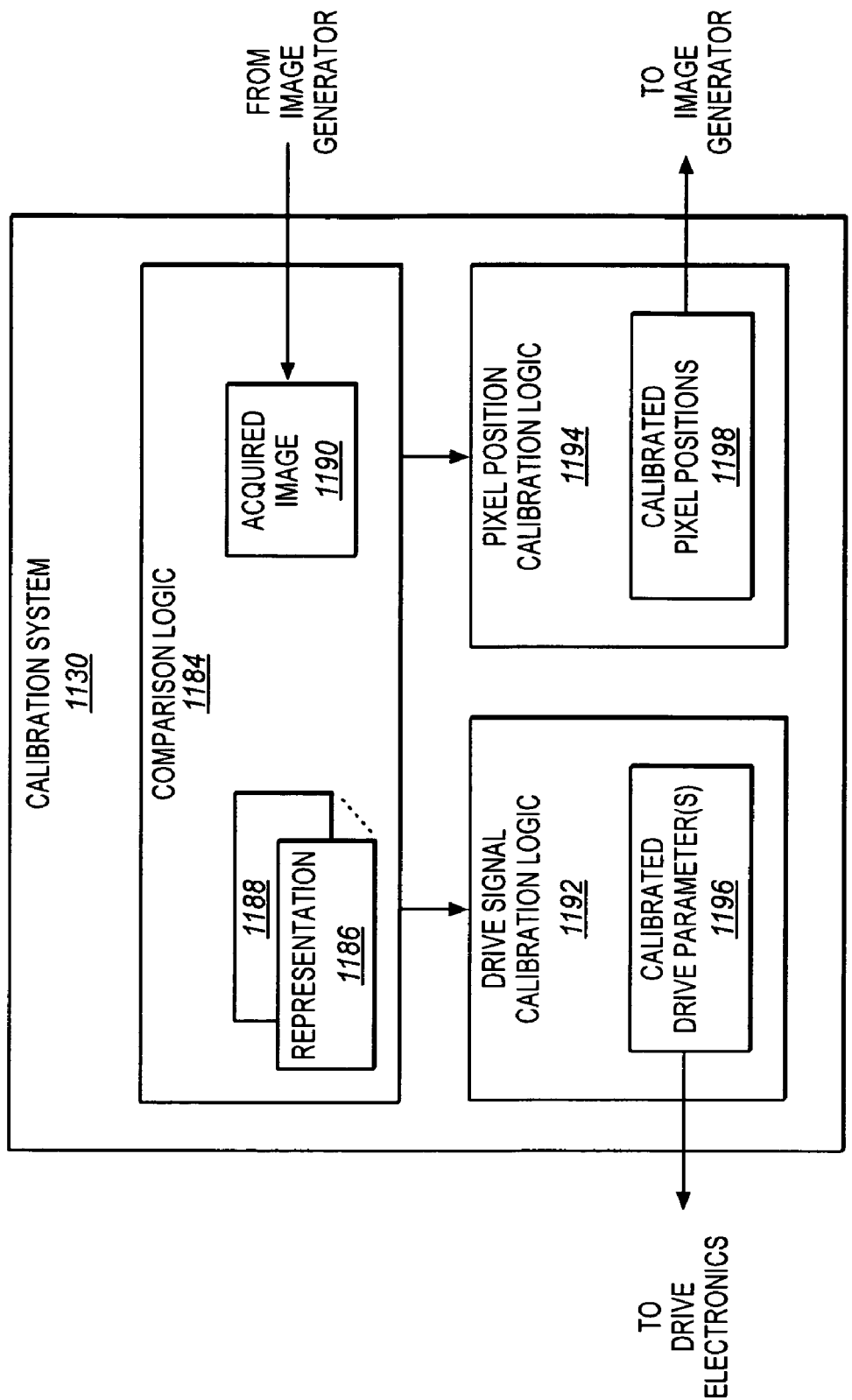
FIG. 11 is a block diagram showing further details of an example calibration system for a scanning beam device, according to one or more embodiments of the invention.

As shown in FIG. 2, the scanning beam device may include a calibration system 230, which may implement one or more calibrations as disclosed herein. FIG. 11 is a block diagram showing further details of an example calibration system 1130 for a scanning beam device, according to one or more embodiments of the invention.

The calibration system includes comparison logic 1184. The comparison logic may compare a representation of a calibration pattern 1186 with an acquired image 1190 of the calibration pattern as disclosed elsewhere herein.

As previously mentioned, the representation of the calibration pattern may include an electronic image or other electronic likenesses of the calibration pattern, or a set of features or characteristics of the calibration pattern (for example, number of circles, size of circles, etc). By way of example, the representation and the acquired image may be accessed from a memory or otherwise received or referenced by the comparison logic. As yet another option, the representation may be a mental representation that is not stored in the scanning beam device, but rather in the thoughts or mind of the practitioner.

As shown, in one or more embodiments of the invention, one or more additional, different representations 1188 may also optionally be available (whether stored or not). By way of example, the different representations may be of different calibration patterns, of the same calibration pattern at a different magnitude of the scan, or of the same calibration pattern under different temperatures or other environmental conditions. In one aspect, multiple calibration patterns may potentially be used to challenge the scanning beam device in different ways, such as, for example, with different patterns, different degrees of difficulty, different drive parameters isolated, different color components isolated, or the like. Different representations may be used for different temperatures, or else the temperature of the scanning optical element may be maintained substantially constant, such as, for example, as disclosed in U.S. Pat. No. 7,680,373. Similarly, different sets of calibration data may be stored for different magnitudes of scan, different environmental conditions, etc., and capability may optionally be included to interpolate between the sets to provide a continuous spectrum of magnitudes of scan or environmental conditions.

The calibration system also includes drive signal calibration logic 1192 and pixel position calibration logic 1194. Each of these logics are coupled with, or otherwise in communication with, the comparison logic. The drive signal calibration logic and pixel position calibration logic may perform drive signal calibration and pixel position calibration, respectively, as disclosed elsewhere herein. In particular, the drive signal calibration logic may determine one or more calibrated drive parameters 1196. These drive parameters may be provided to the drive electronics for subsequent use. In one or more embodiments, the calibrated drive parameters may be stored in a configuration memory as disclosed in U.S. Patent Application 20060072874, although this is not required. The pixel position calibration logic may determine and store or otherwise preserve one or more calibrated pixel or other image positions 1198. These calibrated pixel or other image positions may be provided to, or accessed by, the image generator during generation of subsequent images.

In one or more embodiments of the invention, the logic of the calibration system may include software, such as, for example, sequences of instructions or code modules that may be stored in a memory of the scanning beam device and executed by a controller, processor, or other circuit. For example, the modules may include a comparison module, a drive signal calibration module, and a pixel position calibration module. As another option, in one or more embodiments of the invention, the logic of the calibration system may include hardware, such as, for example, by an application specific integrated circuit (ASIC), field programmable gate array (FPGA), or other circuit. As yet another option, the logic of the calibration system may include a combination of software and hardware.

Figure 12:
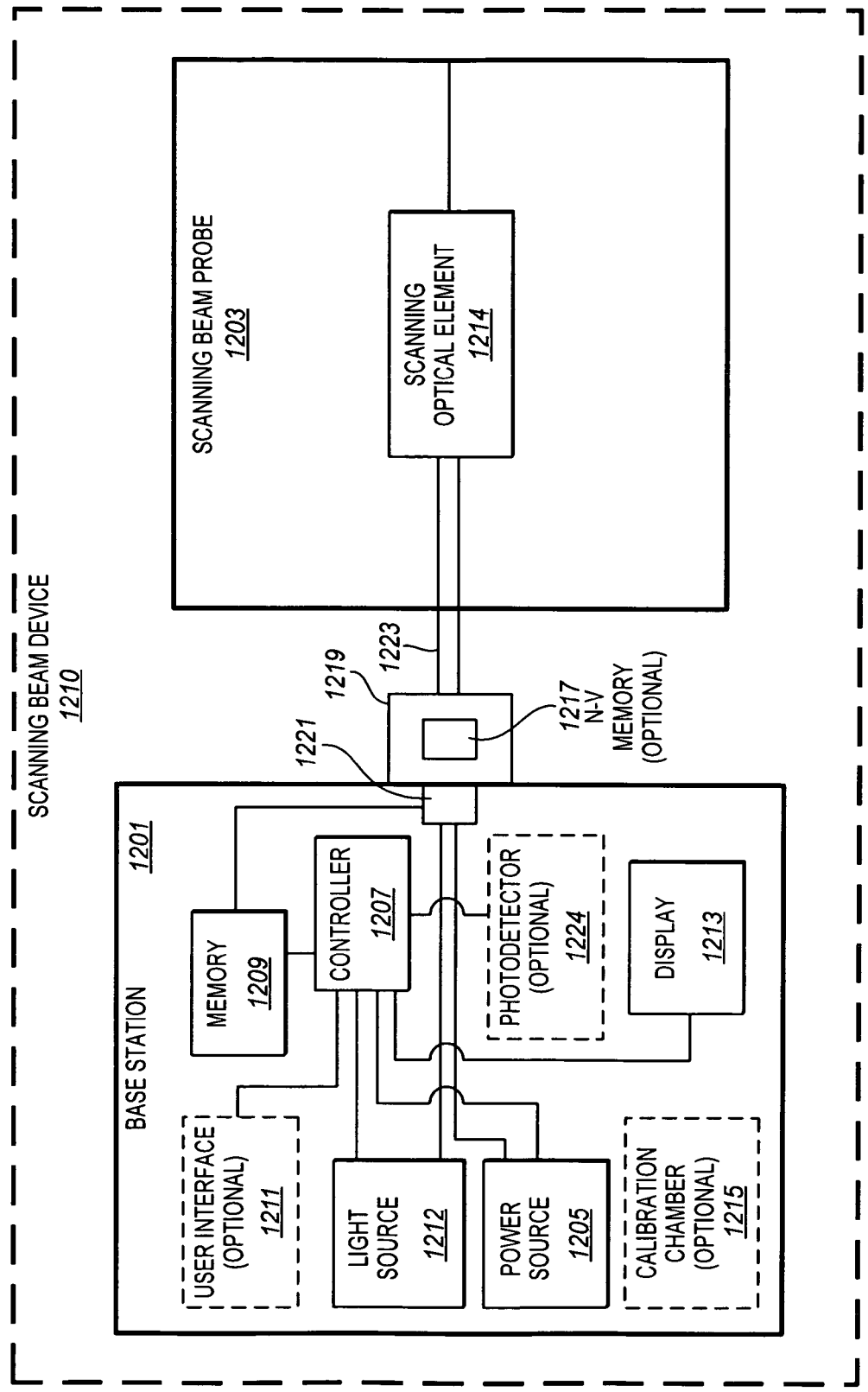
FIG. 12 is a block diagram of an example scanning beam device in which embodiments of the invention may be implemented.

FIG. 12 is a block diagram of an example scanning beam device 1210 in which embodiments of the invention may be implemented. The scanning beam device has a two-part form factor that includes a base station 1201 and a scanning beam probe 1203. Such a two-part form factor tends to be well suited for endoscope and other medical probe implementations. One potential advantage of the two-part form factor is that expensive and/or bulky components may be included in the base station and the probe may be relatively inexpensive and/or small. Other potential advantages are that different types of probes may potentially be used by the same base station and probes may be capable of being removed, for example for cleaning, maintenance, or to be discarded. However, this two-part form factor is not required.

The base station includes a light source 1212, a power source 1205, a controller 1207, and a memory 1209. In one or more embodiments of the invention, the memory may be used to store code modules that may implement at least a portion of a calibration system as disclosed herein and that may be executed by the controller, a separate processor (not shown), or another circuit. The base station includes an optional photodetector 1224. Alternatively, the photodetector may be located in the scanning beam probe. The base station includes an optional user interface 1211. The user interface may include a few buttons, dials, a keyboard, or like interfaces known in the arts. The base station also includes an optional display 1213. As another option, the display may be included separately from the base station or omitted.

The scanning beam probe includes a scanning optical element 1214. In one or more embodiments of the invention, the scanning optical element may include a single, cantilevered, free-end portion of an optical fiber or similar waveguide, and a piezoelectric tube, or other actuator tube to move the optical fiber or waveguide. A detailed example of such a scanning optical element is shown and described in conjunction with FIG. 13. Alternatively, an Electroactive Polymer (EAP) material, a magnetic actuator, an electromagnetic actuator, an electrostatic actuator, a sonic actuator, an electroacoustic transducer, an electromechanical actuator (for example a MEMS), or other type of actuator may be used to move the optical fiber or waveguide.

As another option, in one or more embodiments of the invention, the scanning optical element may include a mirror or other reflective device in an optical path of a beam of light, and an actuator to move the reflective device. As yet another option, a scanning optical element may include a lens or other focusing device that may be moved by an actuator. As still further options, the scanning optical element may include a galvanometer, multiple optical elements moved relative to each other, and the like, and combinations thereof. These various scanning optical elements may also be used in the apparatus of FIG. 2.

The scanning beam probe includes a connector member 1219 that is configured to mate with a connector interface 1221 of the base station. Coupling of the connector member to the connector interface may create electrical and optical paths between the base station and the scanning beam probe. By way of example, the electrical paths may include a power path and a drive signal path, and the optical paths may include an illumination path and potentially a detection path. These paths may be carried through one or more cable 1223.

As shown, the scanning beam probe may include an optional non-volatile (N-V) memory 1217, although this is not required. In one or more embodiments of the invention, the non-volatile memory may be located in the connector member. The non-volatile memory may be used to store calibrated drive parameters and/or calibrated image position information as disclosed herein, although this is not required.

As shown, in one or more embodiments of the invention, the base station of the scanning beam device may include an optional calibration chamber 1215. The calibration chamber may have one or more calibration patterns therein. This may help to protect the one or more calibration patterns from getting dirty, weathered, or otherwise damaged. The calibration chamber may also help to provide a controlled light environment for viewing the calibration pattern. In one aspect, the calibration chamber may have a controlled temperature, or alternatively the probe may be separately capable of maintaining a substantially constant temperature. In one or more embodiments of the invention, the base station may have a means for switching between calibration patterns. For example, a mechanical mechanism may replace one calibration pattern with another. The calibration chamber may have a port thereto to which the scanning beam probe may be coupled during calibration. Such coupling may help to accurately and consistently position the scanning beam probe relative to the calibration pattern. Alternatively, the calibration chamber may optionally be omitted, included in separate manufacturing equipment, or elsewhere.

Figure 13:
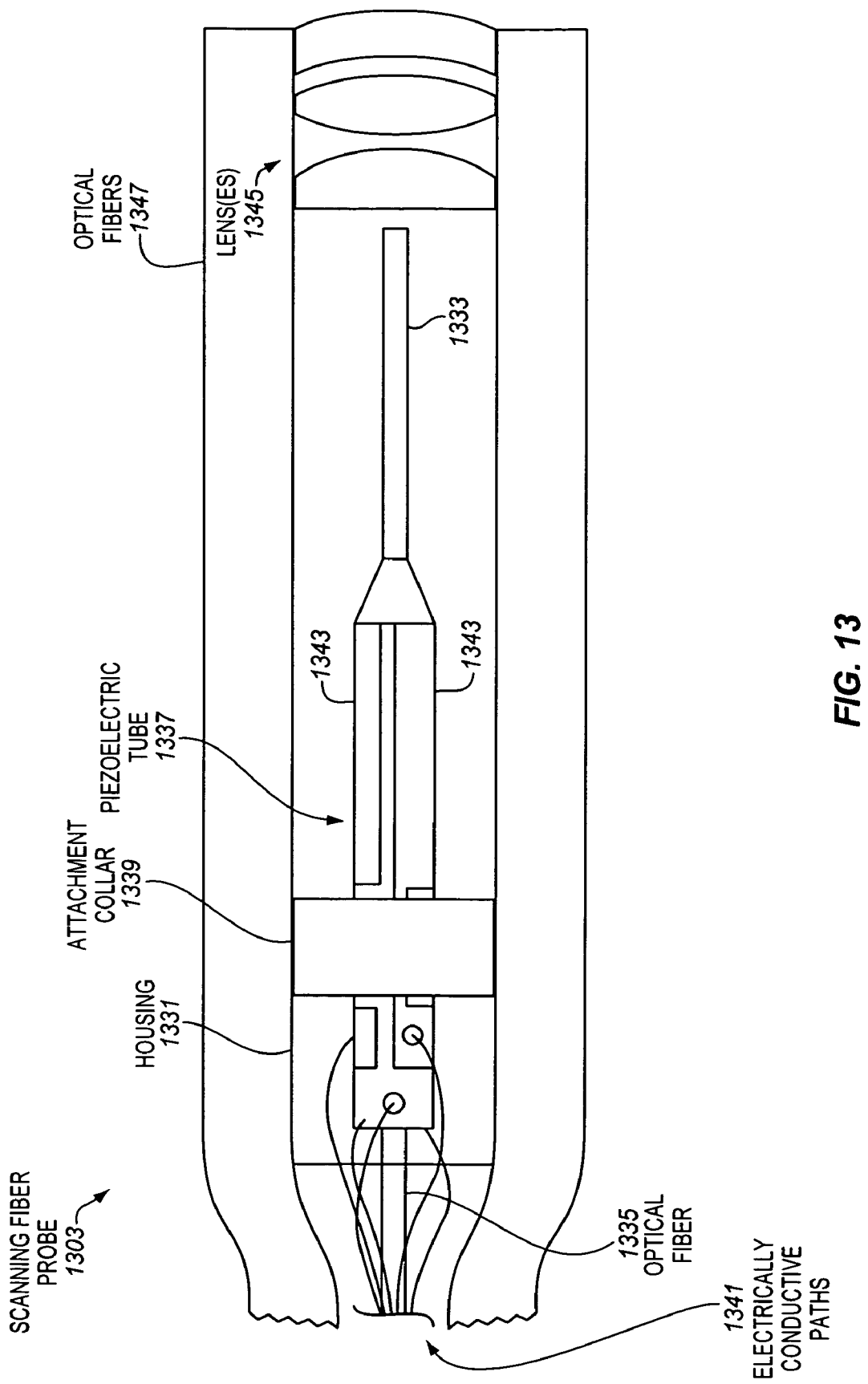
FIG. 13 is a cross-sectional side view of a detailed example of a scanning fiber probe, according to one or more embodiments of the invention.

FIG. 13 is a cross-sectional side view of a detailed example of a scanning fiber probe 1303, according to one or more embodiments of the invention. It is understood that this example is to be construed as merely illustrative, rather than limiting. The particular illustrated probe is well suited for use as an endoscope or other relatively small instrument or probe to be inserted into patients, although in other implementations the design and operation of the probe may vary considerably.

The probe includes a housing 1331. The housing may include stainless steel or other materials suitable for deployment in patients and may be hermetically sealed. The housing may be small or minute. For example, in one or more embodiments of the invention, the housing may be generally tubular, have a diameter or other cross-sectional dimension that is on the order of about 5 millimeters (mm) or less, and have a length that is on the order of about 20 mm, or less.

A free end portion 1333 of an optical fiber 1335 is included within the housing. A piezoelectric tube 1337 is also included within the housing. The piezoelectric tube represents one possible type of actuator tube. In one or more embodiments of the invention, the piezoelectric tube may include a PZT 5A material, although this is not required. The optical fiber is inserted through a generally cylindrical opening in the piezoelectric tube. An attachment collar 1339 may couple the piezoelectric tube with the housing. The piezoelectric tube may be inserted through a tightly fitting generally cylindrical opening through the attachment collar.

A number of wires or other electrically conductive paths 1341 are run from a base station to the proximal end of the probe. The electrically conductive paths may carry electrical signals to the piezoelectric tube. In one or more embodiments, the piezoelectric tube may have four, quadrant metal electrodes 1343 on an outer surface thereof to move the optical fiber in two dimensions. Each of four electrically conductive paths may be soldered to or otherwise electrically coupled with respective ones of four, quadrant-electrodes on the piezoelectric tube. These four paths may carry drive signals to the piezoelectric tube to cause it to scan the optical fiber, for example in an expanding spiral scan pattern. In one or more embodiments, the optical fiber may be scanned at resonance. At resonance the drive signal may be about 90 degrees out of phase relative to the position of the optical fiber. In one or more embodiments, the piezoelectric tube may optionally have a ground electrode on an inside surface thereof. One conductive path may optionally be provided to the ground electrode.

The device includes one or more lenses 1345. The one or more lenses are positioned in an optical path of light directed through the free end portion of the optical fiber. In one or more embodiments of the invention, the one or more lenses may include lenses from Pentax Corporation. Alternatively, other lenses may optionally be used.

In one or more embodiments of the invention, optical fibers 1347 may be included around the outside of the housing to collect backscattered light from a target surface. By way of example, in the particular case of a full-color scanning fiber endoscope, twelve optical fibers may be included around the outside of the housing for collection of light. The optical fibers may collect and convey light back to one or more photodetectors located at a proximal end of the probe or in the base station or elsewhere.

In the description above, for the purposes of explanation, numerous specific details have been set forth in order to provide a thorough understanding of the embodiments of the invention. The particular embodiments described are not provided to limit the invention but to illustrate it. Embodiments may be practiced without some of these specific details. Furthermore, modifications may be made to the embodiments disclosed herein, such as, for example, to the sizes, shapes, configurations, forms, functions, materials, and manner of operation, and assembly and use, of the components of the embodiments. All equivalent relationships to those illustrated in the drawings and described in the specification are encompassed within embodiments of the invention. The scope of the invention is not to be determined by the specific examples provided above but by the claims below. Further, where considered appropriate, terminal portions of reference numerals have been repeated among the figures to indicate corresponding or analogous elements, which may optionally have similar characteristics.

Various operations and methods have been described. The methods have been described in a basic form, but operations may optionally be added to the methods. In some cases, operations may be removed from the methods. In some cases, the operations of the methods may be performed in different order. Many modifications and adaptations may be made to the methods and are possible and contemplated.

Certain operations may be performed by hardware components, or may be embodied in machine-executable instructions, that may be used to cause, or at least result in, a circuit programmed with the instructions performing the operations. The circuit may include a general-purpose or special-purpose processor, or logic circuit, to name just a few examples. The operations may also optionally be performed by a combination of hardware and software.

One or more embodiments of the invention may be provided as a program product or other article of manufacture that may include a machine-accessible and/or readable medium having stored thereon software or other instructions. The medium may provide the instructions, which, if executed by a machine, may result in and/or cause the machine to perform one or more of the operations or methods disclosed herein. Suitable machines include, but are not limited to, scanning beam devices, base stations, endoscope base stations, medical equipment, computer systems, and a wide variety of other devices with one or more processors, to name just a few examples.

The medium may include, a mechanism that stores or otherwise provides information in a form that is accessible by the machine. For example, the medium may optionally include recordable and/or non-recordable mediums, such as, for example, floppy diskette, optical storage medium, optical disk, CD-ROM, magnetic disk, magneto-optical disk, read only memory (ROM), programmable ROM (PROM), erasable-and-programmable ROM (EPROM), electrically-erasable-and-programmable ROM (EEPROM), random access memory (RAM), static-RAM (SRAM), dynamic-RAM (DRAM), Flash memory, and combinations thereof. In one or more embodiments of the invention, an article of manufacture including the machine-readable medium may be included in a kit with one or more of a scanning beam device and instructions for use.

In the claims below, the term "scanning" in "scanning beam device", "scanning optical element", "scanning beam probe", and the like, does not imply that the device or apparatus is in use, or presently in the process of scanning, unless otherwise specified. Rather, the term "scanning" merely implies that the device or apparatus is capable of scanning.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
    acquiring an image of a calibration pattern using a scanning beam device wherein acquiring the image of the calibration pattern comprises scanning a cantilevered optical fiber in a scan pattern including moving the cantilevered optical fiber within a Q factor of a resonant frequency of the cantilevered optical fiber, wherein during the scanning an actual position of the cantilevered optical fiber differs from an expected position of the cantilevered optical fiber;
    comparing the acquired image with a representation of the calibration pattern;
    calibrating the scanning beam device based on the comparison, wherein calibrating the scanning beam device at least partially accounts for the difference between the actual and expected positions of the cantilevered optical fiber during the scanning; and
    repeating said acquiring and said comparing one or more times until a comparison indicates that an acquired image and the representation of the calibration pattern match within a threshold tolerance.

2. The method of claim 1, wherein calibrating the scanning beam device comprises adjusting one or more drive parameters of the cantilevered optical fiber based on the comparison.

3. The method of claim 1, wherein calibrating the scanning beam device comprises preserving calibrated image position information associated with the comparison.

4. The method of claim 3, wherein the calibrated image position information comprises calibrated destination pixel positions, and wherein the destination pixel positions are expected pixel positions adjusted to account for a difference between the acquired image and the representation.

5. The method of claim 3, further comprising:
    scanning a beam over a surface of interest in the scan pattern;
    detecting light at different times during the scan pattern over the surface of interest;
    generating an image of the surface of interest by representing the light detected at each of the different times during the scan pattern at an image position specified in the calibrated image position information.

6. The method of claim 1, wherein calibrating the scanning beam device comprises:
    adjusting one or more drive parameters of the cantilevered optical fiber based on the comparison;

acquiring a second image of either the same or different calibration pattern using the scanning beam device;

comparing the acquired second image with a representation of the calibration pattern used to acquire the second image; and preserving calibrated image position information associated with the comparison associated with the acquired second image.

7. The method of claim 6, further comprising:

scanning a beam over a surface of interest in a scan the scan pattern;

detecting light at different times during the scan pattern over the surface of interest; and generating the image of the surface of interest by representing the light detected at each of the different times at an image position specified in the calibrated image position information.

8. The method of claim 1, wherein acquiring the image of the calibration pattern using the scanning beam device comprises:

scanning a beam over the calibration pattern in the scan pattern;

detecting backscattered light from the calibration pattern at different times during the scan pattern; and generating the image of the calibration pattern by representing the backscattered light detected at each of the different times at a corresponding expected position of the beam for a respective time.

9. The method of claim 1, wherein acquiring the image of the calibration pattern comprises acquiring a multi-colored image of a multi-colored calibration pattern, and wherein comparing comprises comparing different color components of the acquired multi-colored image with corresponding color components of the representation of the calibration pattern.

10. The method of claim 1, wherein acquiring the image of the calibration pattern comprises acquiring a plurality of different color component images of a black and white calibration pattern, and wherein comparing comprises comparing each of the plurality of different color component images with the representation of the black and white calibration pattern.

11. The method of claim 1, further comprising, prior to acquiring the image, coupling a scanning beam probe of the scanning beam device with a port of a calibration chamber of the scanning beam device, the calibration chamber having the calibration pattern therein.

12. The method of claim 1, further comprising, after calibrating the scanning beam device, inserting a scanning beam probe of the scanning beam device into a patient.

13. The method of claim 1, wherein comparing the acquired image with the representation of the calibration pattern comprises mapping a feature in the acquired image to known coordinates of a corresponding feature in the representation of the calibration pattern.

14. An article of manufacture comprising:

a machine-readable medium selected from a floppy diskette, an optical storage medium, an optical disk, a CD-ROM, a magnetic disk, a magneto-optical disk, a read only memory (ROM), a programmable ROM (PROM), an erasable-and-programmable ROM (EPROM), an electrically-erasable-and-programmable ROM (EEPROM), a random access memory (RAM), a static-RAM (SRAM), a dynamic-RAM (DRAM), and a Flash memory, the machine-readable medium storing instructions that if executed result in a machine performing operations including, comparing an image of a calibration pattern, which has been acquired with a scanning beam device, with a representation of the calibration pattern;

calibrating the scanning beam device based on the comparison, wherein calibrating the scanning beam device at least partially accounts for a difference between an actual and an expected position of a scanned beam used to acquire the image of the calibration pattern with the scanning beam device; and repeating said comparing and said calibrating one or more times until a comparison indicates that an image acquired with the scanning beam device and the representation of the calibration pattern match within a threshold tolerance.

15. The article of manufacture of claim 14, wherein the instructions that if executed result in the machine calibrating the scanning beam device based on the comparison further comprise instructions that if executed result in the machine performing operations comprising:

adjusting one or more drive parameters of a scanning optical element of the scanning beam device based on the comparison.

16. The article of manufacture of claim 14, wherein the instructions that if executed result in the machine calibrating the scanning beam device based on the comparison further comprise instructions that if executed result in the machine performing operations comprising:

storing calibrated image position information associated with the comparison.

17. The article of manufacture of claim 16, wherein the instructions further comprise instructions that if executed result in the machine performing operations comprising:

generating an image of a surface of interest by representing light that has been detected at each of a plurality of different times during a scan of a beam over the surface of interest in a scan pattern at an image position specified in the calibrated image position information.

18. The article of manufacture of claim 14, wherein the instructions that if executed result in the machine comparing the acquired image with the representation of the calibration pattern further comprise instructions that if executed result in the machine performing operations comprising:

mapping a feature in the acquired image to known coordinates of a corresponding feature in the representation of the calibration pattern.

19. An apparatus comprising:

a light source;

a scanning optical fiber to receive light from the light source, the scanning optical fiber to vibrate within a Q factor of a resonant frequency and to scan a beam over a calibration pattern in a scan pattern;

a photodetector to detect light backscattered from the calibration pattern at different times during the scan pattern;

image generation logic to generate an image of the calibration pattern by representing the backscattered light detected at each of the different times at a corresponding expected position of the beam for a respective time;

a calibration system including comparison logic to compare the image with a representation of the calibration pattern and to calibrate the apparatus to at least partially account for a difference between the expected positions of the beam and actual positions of the beam during the scan pattern, wherein the calibration system is configured to repeat comparison of images generated by the image generation logic one or more times until a comparison indicates that an image and the representation of the calibration pattern match within a threshold tolerance.

20. The apparatus of claim 19, further comprising drive signal calibration logic in communication with the comparison logic, the drive signal calibration logic to adjust one or more drive parameters of the scanning optical fiber based on the comparison.

21. The apparatus of claim 19, further comprising pixel position calibration logic to store calibrated image position information associated with the comparison.

22. The apparatus of claim 21, wherein the pixel position calibration logic comprises logic to generate an image of a surface of interest by representing light that has been detected at each of a plurality of different times during a scan of a beam over the surface of interest in the scan pattern at an image position specified in the calibrated image position information.

23. The apparatus of claim 19, further comprising a chamber having the calibration pattern therein.

24. The apparatus of claim 19, wherein the apparatus comprises an endoscope.

25. The apparatus of claim 19, wherein the calibration pattern does not comprise a photosensitive position sensor.

* * * * *